(12) United States Patent
Khoo et al.

(10) Patent No.: US 12,274,835 B2
(45) Date of Patent: Apr. 15, 2025

(54) EXTENDED DWELL AND MIDLINE CATHETERS AND RELATED METHODS

(71) Applicant: B. Braun Melsungen AG, Melsungen (DE)

(72) Inventors: Teng Lip Khoo, Pulau Pinang (MY); Lilian Zhi Ling Lew, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 830 days.

(21) Appl. No.: 17/296,912

(22) PCT Filed: Nov. 28, 2019

(86) PCT No.: PCT/EP2019/082867
§ 371 (c)(1),
(2) Date: May 25, 2021

(87) PCT Pub. No.: WO2020/109448
PCT Pub. Date: Jun. 4, 2020

(65) Prior Publication Data
US 2022/0032008 A1    Feb. 3, 2022

Related U.S. Application Data

(60) Provisional application No. 62/772,195, filed on Nov. 28, 2018.

(51) Int. Cl.
*A61M 25/01* (2006.01)
*A61M 25/00* (2006.01)
(Continued)

(52) U.S. Cl.
CPC .... *A61M 25/0113* (2013.01); *A61M 25/0014* (2013.01); *A61M 25/0606* (2013.01); *A61M 25/09041* (2013.01)

(58) Field of Classification Search
CPC .......... A61M 25/0606; A61M 25/0618; A61M 25/0631; A61M 25/0113; A61M 25/0014; A61M 25/09041
See application file for complete search history.

(56) References Cited

U.S. PATENT DOCUMENTS

| 8,932,258 B2 | 1/2015 | Blanchard et al. |
| 2004/0055926 A1* | 3/2004 | Duffy .................. A61M 25/002 604/536 |

(Continued)

FOREIGN PATENT DOCUMENTS

| WO | WO 2015/023358 A1 | 2/2015 |
| WO | WO 2015/168655 A2 | 11/2015 |

OTHER PUBLICATIONS

International Search Report and Written Opinion on corresponding PCT application (PCT/EP2019/082867) from International Searching Authority (EPO) dated Mar. 31, 2020.

*Primary Examiner* — Michael J Tsai
*Assistant Examiner* — Neeraja Gollamudi

(57) ABSTRACT

Extended dwell catheter assembly allows for one-handed operation by a physician such that the physician may continue to operate a visualization tool with the other hand throughout the catheterization process using the extended dwell catheter assembly. The catheter assembly can have stacked push tags to prevent false activations and to provide a manipulation means in the correct order of actuation.

25 Claims, 21 Drawing Sheets

(51) Int. Cl.
*A61M 25/06* (2006.01)
*A61M 25/09* (2006.01)

(56) References Cited

U.S. PATENT DOCUMENTS

| | | | |
|---|---|---|---|
| 2014/0081210 A1* | 3/2014 | Bierman | A61M 25/0043 604/523 |
| 2015/0231364 A1* | 8/2015 | Blanchard | A61M 25/0618 604/164.08 |
| 2016/0331938 A1 | 11/2016 | Blanchard et al. | |
| 2018/0296799 A1 | 10/2018 | Horst et al. | |

* cited by examiner

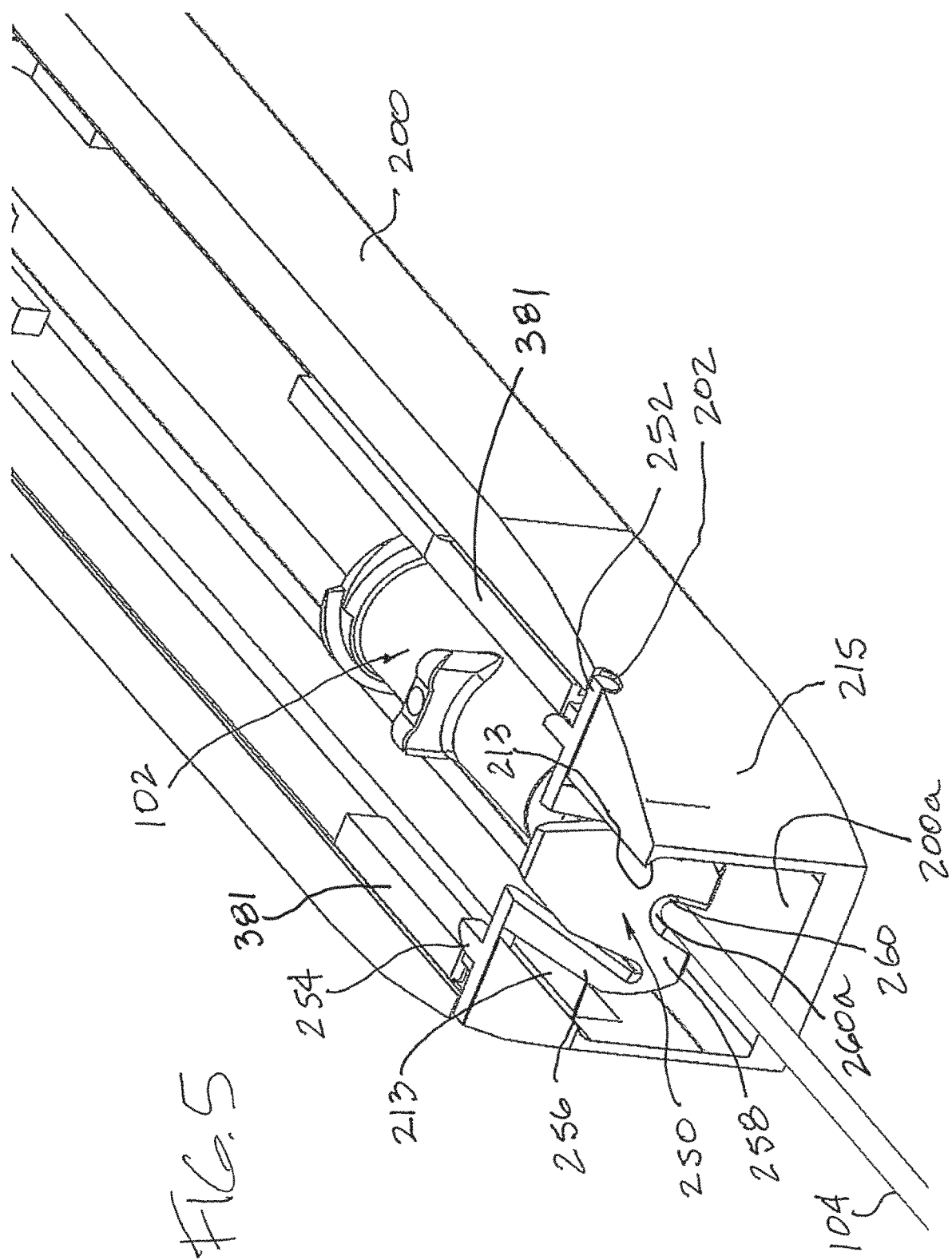

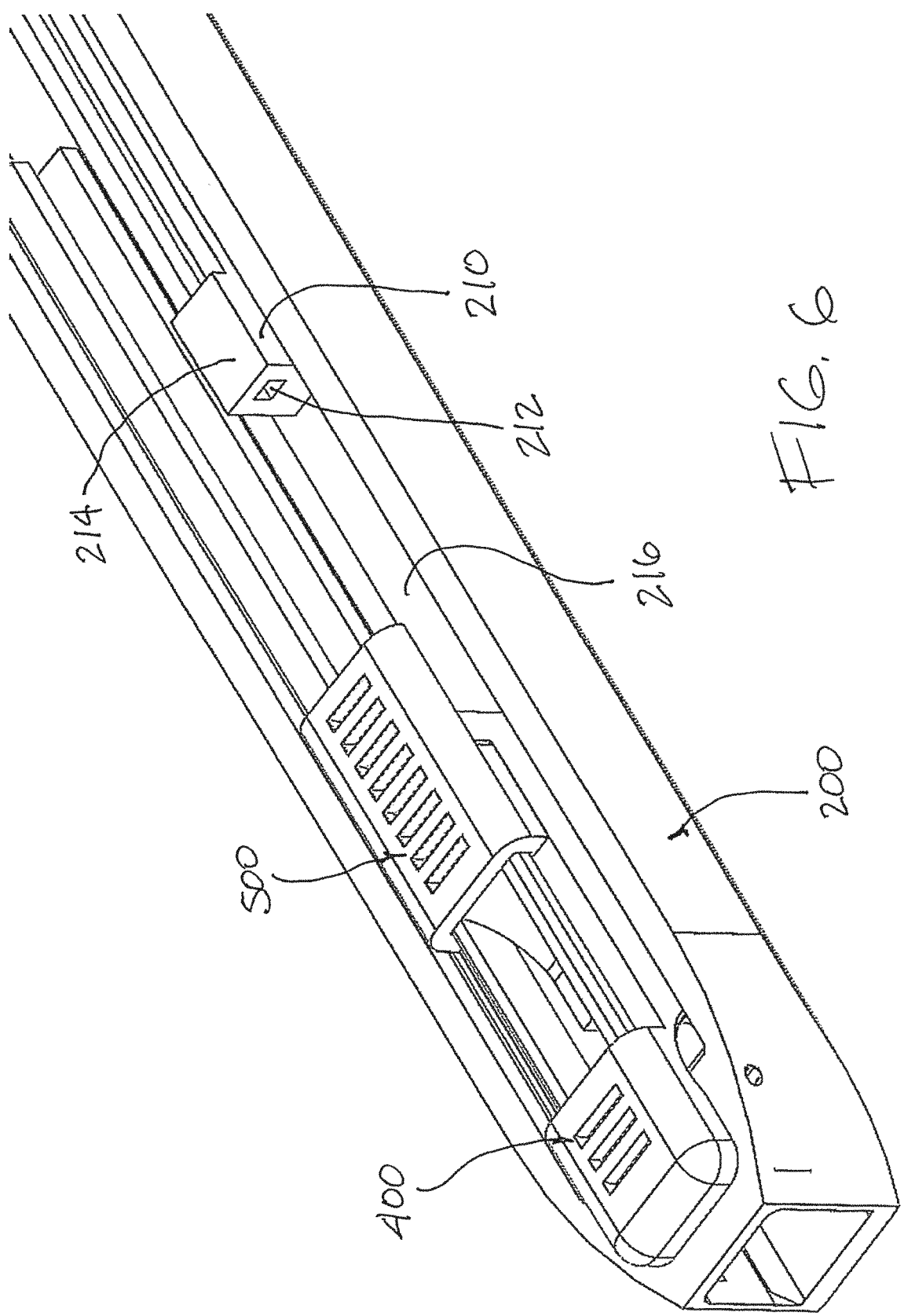

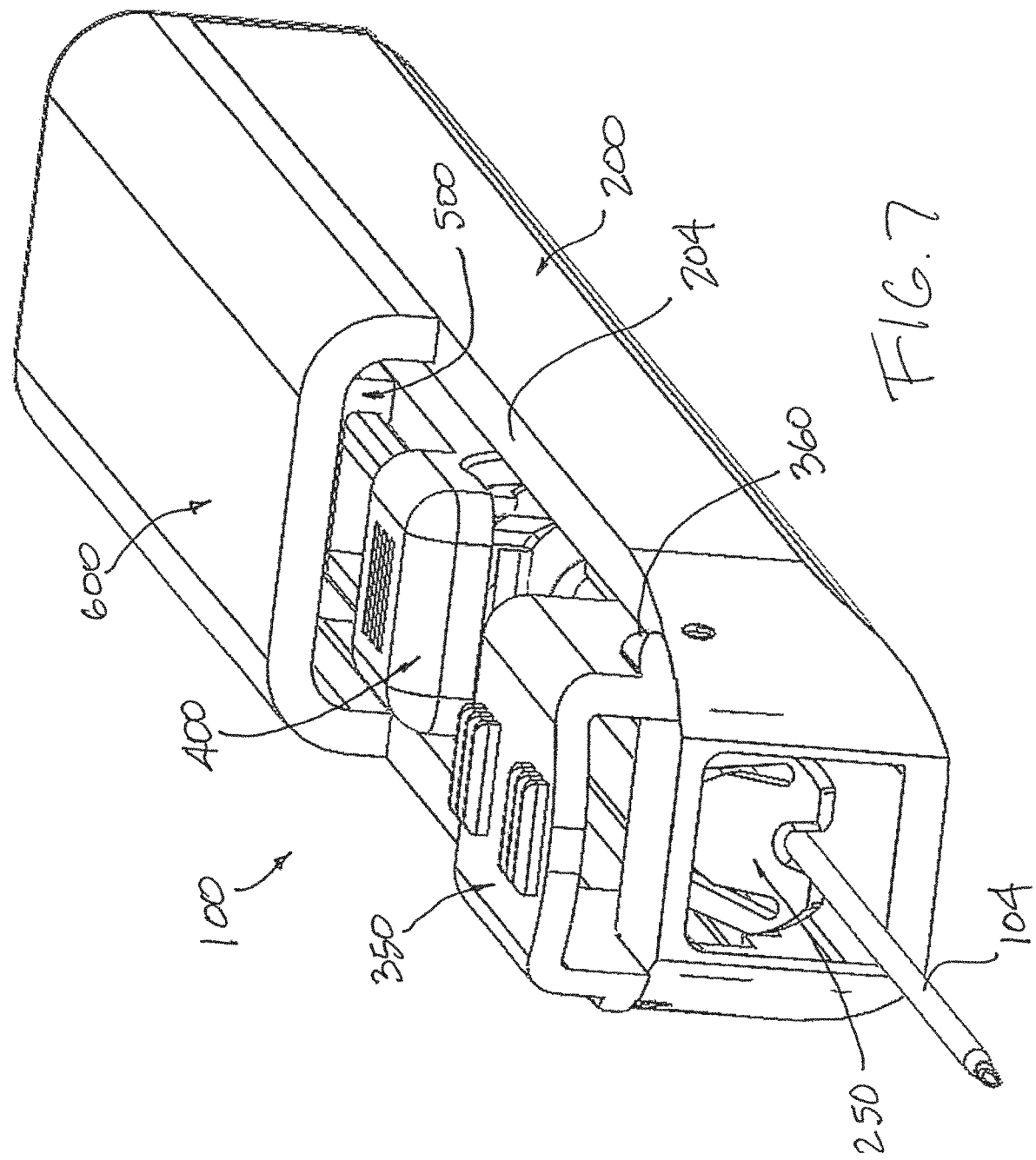

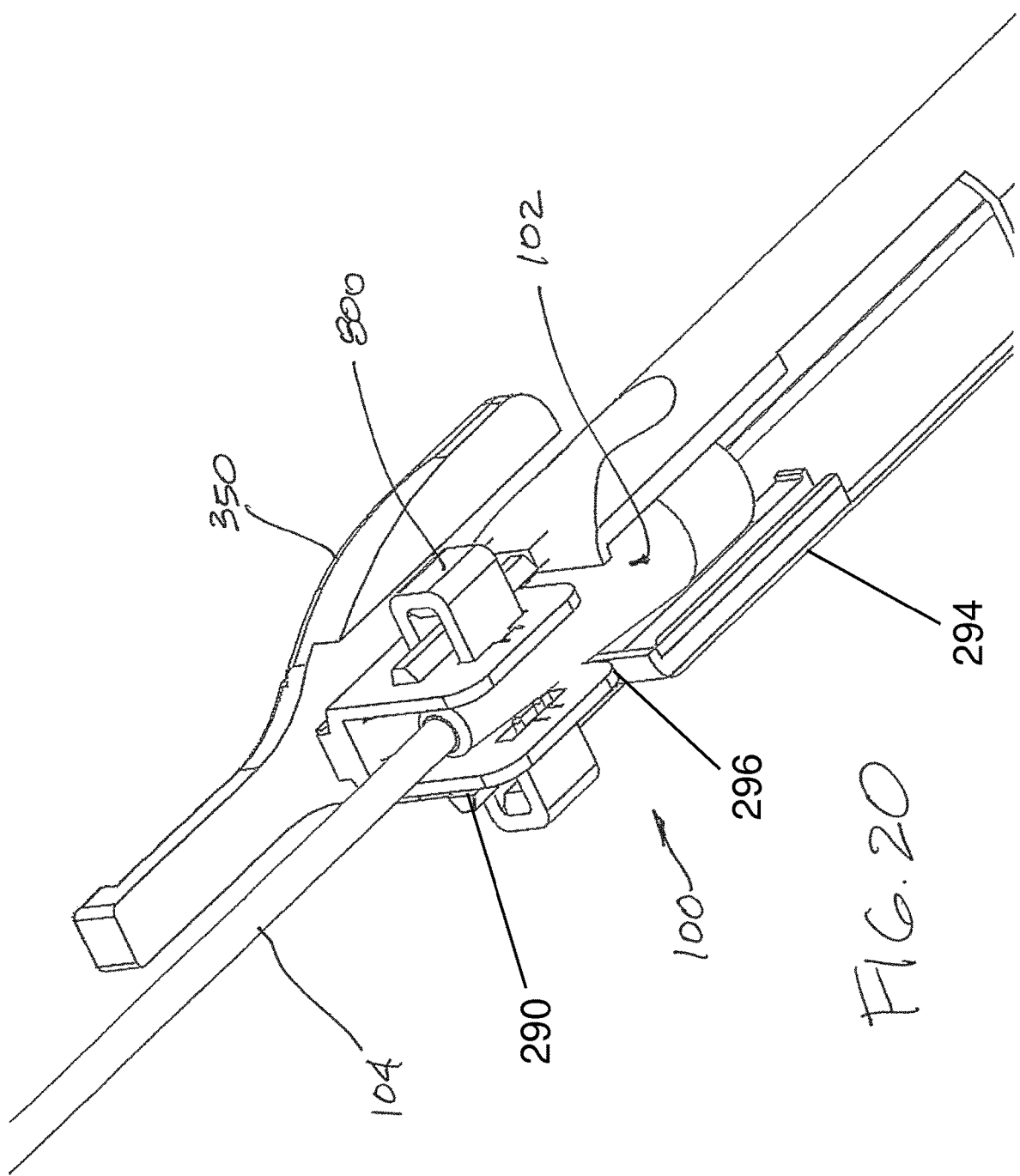

EXTENDED DWELL AND MIDLINE CATHETERS AND RELATED METHODS

FIELD OF ART

The disclosed invention generally relates to needle devices and intravenous (IV) infusion devices, including IV catheters. In particular, IV catheter assemblies having a one-handed operation for actuation are disclosed.

BACKGROUND

IV catheters are commonly used for a variety of infusion therapies, including infusing fluids into a patient, withdrawing blood from a patient, or monitoring various parameters of the patient's vascular system. Catheters are typically connected to a catheter adapter that accommodates the attachment of IV tubing to the catheter. Blood control catheters include an internal blood control valve that is opened by the insertion of a male Luer or another object into a proximal end of the catheter adapter. Non-limiting examples of blood control valves are disclosed in United States Patent Application Publication No. 2011/0046570, filed Aug. 20, 2009, titled "Systems and Methods for Providing a Flushable Catheter Assembly." Following placement of the catheter into the vasculature of a patient, an IV fluid source can be connected to the catheter adapter or catheter hub, opening the blood control valve. Thus connected, fluid from the IV source can begin flow into a patient through the catheter.

As is well known in the art, typical blood pressure is 10 to 20 centimeters of water. Infusion bags are usually placed about 100 cm above the patient's heart to direct flow into the patient. At roughly that height, the pressure exerted by the fluid from the infusion bag is much greater than the blood pressure of the patient and therefore can flow into the patient.

For patients with difficult to access veins, extended dwell catheters can be used to aid in Difficult Intravenous Access (DIVA). An extended dwell catheter is a midline catheter that may be considered a peripherally inserted catheter. However, a typical midline catheter is configured to be inserted in a larger vein than those used for standard I.V. therapy. The recommended insertion site for the midline catheter is the basilic, cephalic, or median vein in the antecubital fossa. For DIVA patients, a physician can use visualization equipment to aid in identification of deep veins for catheter access. In that case, an extended dwell catheter will provide a longer length and a more flexible catheter for insertion into the patient. With the addition of a guidewire, this can help to reduce the chances of the catheter becoming kinked.

SUMMARY

The devices and methods of the present disclosure can increase first stick success through a one-handed technique and can provide an intuitive design, which requires minimal training for physicians. The one-handed technique provides the option for a physician or user to simultaneously perform the catheterization process with one hand while using a visualization tool, such as an ultrasound, with the other hand. Alternatively, the user of the device can rely on a second user to operate the visualization tool while the first user operates the midline catheter.

Aspects of the present invention include a catheter assembly comprising: a housing; a catheter hub; catheter tube coupled to the catheter hub, the catheter tube defining a catheter axis; a needle projecting through the catheter tube; a first catheter push tag for moving the catheter hub relative to the housing, wherein a portion of the first catheter push tag can be arranged to be activated in a ready to use state.

The housing can have spaced apart sidewalls. The sidewalls can form a frame or body of the housing.

In an alternative embodiment, a guidewire push tag is pushed or moved to advance a guidewire after initial puncture of the needle tip and the tip of the catheter tube into the vein and prior to moving the first catheter push tag to advance the catheter hub, and hence further moving the catheter tube into the vein. In other words, embodiments of the present midline device can be practiced without a guidewire and a guidewire push tag.

In yet other aspects of the present invention, a midline device or an extended dwell peripheral IV device is provided and wherein the device has multiple moving parts for placing a catheter tube in a vein of a patient, said multiple moving parts being arranged sequentially by stacking different tags associated with the different moving parts. The different moving parts can be configured to move serially or sequentially, one after another. The serially movable configuration of the multiple moving parts can be configured to properly move one part of the device before the next part of the device is moved for proper device operation.

In an example, the serially movable configuration of the multiple moving parts can be configured as an aid to direct a user on the appropriate way to operate the device to avoid confusion. The serially movable configuration can prevent early activation of one part of the catheter device before another part of the device.

In an example, the serially movable configuration of the multiple moving parts can be arranged with a distally most positioned moving part, then a next distally most positioned moving part, then a next distally most positioned moving part.

In some examples, the serially movable configuration of the multiple moving parts can be arranged with two movable push tags that are arranged at approximately the same distal position on the device, but wherein one is located superjacent or above the other.

In an example, the multiple movable push tags can each have a body with a surface configured for pushing, moving, or otherwise manipulated by a user to move the push tags. For example, the user can place a digit onto the surface and slide the push tag in the distal direction.

The various push tags can be associated with specific functions and can be identified by their specific functions. Generically, they can all be referred to simply as push tags.

In an example, a first moving part, such as the first push tag, is exposed but one or more additional parts, such as one or more additional push tags, to be moved are covered until the first of the moving parts is moved. After the first of the moving parts is moved, the second of the moving parts can be exposed by the vacated or moved first moving part to then be moved by a user. Optionally, a third of the moving parts is then exposed for moving by the user after movement of the second moving part. Optionally, a fourth of the moving parts is then exposed for moving by the user after movement of the third moving part. Optionally, a fifth of the moving parts is then exposed for moving by the user after movement of the fourth moving part.

In an example, the moving parts, such as movable push tags, are configured to move serially by staggering different push tags so that one push tag has to move before the next push tag can move, and so forth. In a particular example, a guidewire push tag is first moved, which then exposes a first catheter push tag. The first catheter push tag is then moved to expose a second catheter push tag.

The guidewire push tag, the first catheter push tag, and the second catheter push tag can generally be referred to as a first push tag, a second push tag, and a third push tag.

The second catheter push tag, or generally called the third push tag, can then move to separate a catheter hub from a housing of the extended dwell peripheral IV device. In other examples, a fourth push tag and/or a fifth push tag are moved after the third push tag is moved. For example, the fourth push tag can further assist in pushing the catheter hub. The fifth push tag can separate the housing into two or more housing sections.

In another example, the moving parts can be configured to move serially by staggering different push tags so that one push tag has to move before the next push tag can move, and so forth. In a particular example, the housing is first moved to insert the needle and the tip of the catheter tube into the vein. Blood flash back is observed, such as through a notch near the needle tip or an elongated groove extending lengthwise of the needle between the needle and the catheter tube.

Once blood flash back is confirmed, the housing is held steady and the guidewire push tag is first moved, first among the various movable components mounted to the housing, which then exposes the first catheter push tag. The first catheter push tag is then moved to expose the second catheter push tag. The second catheter push tag, or generically the third push tag to be moved, can then move to separate a catheter hub from a housing of the extended dwell peripheral IV device. In other examples, a fourth push tag and/or a fifth push tag are moved after the third push tag is moved. For example, fourth and fifth push tags can be used to help push the catheter hub away from the housing and to separate the housing into two pieces or more pieces.

In yet another example, a guidewire and a guidewire push tag are not incorporated with the midline device. Without the guidewire and without the guidewire push tag, the midline device can have at least two push tags, which can include a first push tag and a second push tag. The first push tag can be a first catheter push tag and the second push tag can be a second catheter push tag, and wherein the first catheter push tag is first moved to expose the second push tag, which can then be moved by a user.

In a particular example without a guidewire and without a guidewire push tag, the first push tag is located next to a cover. The cover can be fixed or stationary relative to the body of the housing. The second push tag can be hidden or stacked under the cover so that the second push tag is not accessible until either the cover is removed or the second push tag is first exposed, such as moved away from the coverage of the cover. For example, after sticking a patient with the needle and inserting the tip of the catheter tube into the vein, the first push tag is distally advanced to further advance the catheter tube over the needle. Once the first push tag is advanced in the distal direction, the movement moves the second push tag and exposes the second push tag from the coverage of the cover. The second push tag can then be moved to move the catheter hub relative to the housing.

In an example, the first catheter push tag is fixed to a body section having two sidewalls. The second catheter push tag is mounted to the body section so that movement of the body section when the first push tag moves also moves the second catheter push tag.

The catheter assembly can further comprise a guidewire projecting through the needle; and a guidewire push tag for moving the guidewire relative to the housing. The guidewire can be optional and may be incorporated when the length of the needle and catheter tube warrants its use.

In an example, the needle can be secured to a needle holder. The needle holder can be called a retention block. The retention block can have a through bore. The retention block can be fixed to the housing. For example, the retention block can extend from one of the sides of the housing and located inside the cavity of the housing. The needle can attach to the retention block and extend out a first end of the bore. The guidewire can project through the second end of the bore and through the lumen of the needle.

The guidewire can slide or move relative to the needle. A guidewire holder can be used to secure or hold an end of the guidewire. The guidewire holder can move when moving the guidewire push tag. The guidewire holder can be configured to abut the retention block that holds the needle to limit distal advancement of the guidewire.

The catheter assembly can further comprise a second catheter push tag to release the catheter hub from coupling with the housing. The first catheter push tag can move the catheter hub while the second catheter hub can further move the catheter hub to separate from the housing.

The second catheter push tag can be slidably coupled to the first catheter push tag. The first and second catheter push tags can move together and can move relative to one another.

In an example, when the first catheter push tag is moved, the movement of the first catheter push tag also moves the second push tag to expose the second push for moving by a user.

A guidewire push tag, when incorporated, can prevent user manipulation of the first catheter push tag in a ready to use state. In an example, the guidewire push tag, when incorporated, covers or hides the first catheter push tag from user access. Thus, the guidewire push tag is to configured to be moved first to expose the first catheter push tag. Once exposed, the first catheter push tag is accessible by the user to then move by the user.

The various push tags can be slidably mounted to a housing. The housing can have cooperating surfaces or structure to support the various push tags and allow the various push tags to slide. In an example, the second catheter push tag is slidably mounted to a housing portion of the first catheter push tag. Thus, in an example, the second catheter push tag can be located within the interior of the housing but does not touch or contact the housing. In alternative embodiments, the second catheter push tag can have guide posts or surfaces that cooperate with the housing to facilitate guiding the second catheter push tag as it moves in the distal direction.

In an example, the guidewire push tag, when incorporated, overlies the first catheter push tag and covers the first catheter push tag. In a particular example, the guidewire push tag is move in a distal direction to expose the first catheter push tag. The first catheter push tag can remain in place while the guidewire push tag is moved. Movement of the guidewire push tag can be in the distal direction. In some examples, movement of the guidewire push tag can minimally move the first catheter push tag but not significantly.

Movement of the first catheter push tag can be in the distal direction.

Movement of the second catheter push tag can be in the distal direction.

Movement of the first catheter push tag can be prevented by the guidewire push tag covering and preventing access to the top surface of the first catheter push tag.

Access is understood to mean usable access, such as placement of a digit onto a surface of the push tag, and not just visual access.

Movement of the first catheter push tag can move a structure that connects the first catheter push tag with the second catheter push tag. The structure can be a body section having sidewalls. The sidewalls can have surface contours, such as track, guide and/or a groove rail. The second catheter push tag can have a cooperating surface for interacting with the track or rail.

The second catheter push tag can be covered until after the first catheter push tag is moved in the distal direction.

At least one push tag can be mounted to a housing. The housing can prevent use manipulation of a second catheter push tag in a ready to use state. In an example, a cover attached to a frame of the housing can be part of the overall housing. The cover can be utilized to cover the second catheter push tag when a first catheter push tag is in its proximal position, prior to the first catheter push tag being moved by a user.

In an example, a midline device or an extended dwell peripheral IV device is provided with a guidewire push tag, a first catheter push tag, and a second catheter push tag. In a particular example, the guidewire push tag covers the first catheter push tag from being touched by a user and a cover or cap mounted with the frame of the housing covers the second catheter push tag from being touched by a user in the first or ready to use position of the device.

The first catheter push tag can be unobscured after user manipulation of the guidewire push tag; and wherein the second catheter push tag can be unobscured after user manipulation of the first catheter push tag.

The first catheter push tag, the guidewire push tag, and the second catheter push tag can be stacked within the housing such that only the guidewire push tag is accessible in the ready to use state.

Aspects of the present disclosure include a method of assembling a catheter assembly, the method comprising assembling a first catheter push tag to a housing, wherein a portion of the first catheter push tag is obscured in a ready to use state; placing a catheter hub in sliding contact with the first catheter push tag; coupling a catheter tube to the catheter hub; projecting a needle through the catheter tube.

The method can further comprise projecting a guidewire through the needle and placing a guidewire push tag into the housing to move the guidewire relative to the housing.

The method can comprise coupling a guidewire to a guidewire push tag and positioning the guidewire push tag to overlie the first catheter push tag.

The method can comprise placing a needle into the housing and slot the needle into a retention holder or block.

The method can comprise mounting a first catheter push tag coupled with a second catheter push tag to the housing.

The method can comprise placing a catheter hub coupled with a catheter tube in sliding contact with the first catheter push tag so that movement of the first catheter push tag will cause the catheter hub to move.

The method can comprise placing the needle through the catheter hub and the catheter tube.

The method can comprise projecting a guidewire through the needle and placing a guidewire push tag into the housing to move the guidewire relative to the housing.

After initial insertion of the needle tip for vascular access and if the device incorporates a guidewire, the guidewire push tag can be advanced by a user to advance the guidewire relative to the needle tip. As is well understood in the industry, the guidewire can be utilized to enter tight spaces or to assist in inserting, positioning, and/or moving the catheter deeper into the vein.

The method can further comprise mounting a second catheter push tag relative to the first catheter push tag, said second catheter push tag can be configured to release the catheter hub from the housing.

The second catheter push tag can be slidably coupled to the first catheter push tag.

The guidewire push tag can prevent user manipulation of the first catheter push tag in a ready to use state.

The housing, such as the cover attached to the frame, can prevent user manipulation of the second catheter push tag in a ready to use state. The second catheter push tag is accessible for user manipulation after the first catheter push tag is advanced by a user to advance the catheter hub and the second catheter push tag by a release amount or distance in the distal direction to then expose the second catheter push tag from the cover. Once exposed from the coverage or shielding of the cover, the second catheter push tag can be manipulated by the user.

The first catheter push tag can be unobscured after user manipulation of the guidewire push tag; and the second catheter push tag can be unobscured after user manipulation of the first catheter push tag.

Aspects of the invention further include a catheter assembly comprising: a housing having spaced apart walls; a catheter hub located within the housing; a catheter tube coupled to the catheter hub, the catheter tube defining a catheter axis; a needle projecting through the catheter tube; and a catheter activation device comprising a first push tag having a surface for pushing to move the catheter hub relative to the housing and a second push tag having a surface for pushing to move the catheter hub relative to the housing, wherein the first and second push tags are movable with one another to move the catheter hub from a first position to a second position within the housing and the first and second push tags are movable relative to one another for moving the catheter hub from the second position to a third position; and wherein the first and second push tags are spaced from one another a first distance in the first position and are spaced from one another a second distance in the second position, which is less than the first distance.

The surface of the second push tag can be obscured by the housing in a ready to use state.

A cover can attach to the housing to obscure or cover the surface of the second push tag.

A guidewire can project through the needle and a guidewire push tag can slidably be mounted within the housing for moving the guidewire relative to the needle.

The second push tag can be covered by a cover attached to the housing, the cover can comprise a surface that covers the second push tag such that the second push tag is not accessible until after activation of the first push tag.

The second push tag can be slidably coupled to the first push tag to move with the first push tag and slidable relative to the first push tag.

The first push tag, the guidewire push tag, and the second push tag can be stacked within the housing such that only the guidewire push tag is accessible by a user in the ready to use state.

A support piece can be pivotably connected to the housing. The support piece can be located at a distal end of the housing. The support piece can have a split to deflect or expand at a location between two pivot arms. The support piece can have at least one rotation stop to contact or abut against the housing to resist rotation. The guidewire push tag can push on the rotation stop to allow the support piece to rotate.

The support piece can be deflectable by the guidewire push tag.

The support piece can comprise two mounting arms defining a rotational axis.

Aspects of the invention further include a method of assembling or making a catheter assembly. The method can comprise assembling a catheter activation device comprising a first push tag having a surface and a second push tag having a surface to a housing, said housing having spaced apart sidewalls; placing a catheter hub in sliding communication with the first push tag and the second push tag; coupling a catheter tube to the catheter hub; projecting a needle through the catheter tube; and wherein the first push tag and the second push tag are movable with one another to move the catheter hub from a first position to a second position and the first push tag and the second push tag are movable relative to one another to move the catheter hub from the second position to a third position.

The method can further comprise projecting a guidewire through the needle and mounting a guidewire push tag to the housing to move the guidewire relative to the housing.

The method can further comprise mounting the second push tag in sliding communication with groove rails located on sidewalls of the first push tag.

The method can further comprise engaging rail protrusions of the second push tag with groove rails of the first push tag.

The method can further comprise mounting the needle to a retention block and projecting the guidewire through the retention block and through the needle.

An extended dwell catheter assembly, or catheter assembly or assembly for short, can include a catheter hub, a cannula or needle, a catheter tube, a housing, a support piece, a bracket, a guidewire push tag, a guidewire, a catheter push tag, an integrated catheter push tag, and a back cover. The catheter push tag can be referred to as a first catheter push tag and the integrated catheter push tag can be referred to as a second catheter push tag.

Optionally, the extended dwell catheter assembly can have fewer than the various components shown in FIG. 1. For example, multiple components can be integrated into a single structure that performs multiple steps or functions. As another example, the guidewire and guidewire push tag can be omitted where the lengths of the needle and catheter do not require the added support or guidance of the guidewire. As still yet another example, instead of three or more push tags, the assembly can incorporate only two push tags.

The side of the housing with the support piece can be understood as a distal direction or distal end and the side of the housing with the back cover can be understood as a proximal direction or proximal end. The distal direction can also be viewed as the direction towards the tip of the cannula and the proximal direction is the opposite direction. In this way, the farthest end tip of the cannula opposite the catheter hub can be understood as a distal end or direction.

The back cover can be understood as a top side or top end of the catheter assembly. The cannula of the present disclosure can be with or without flashback features, such as a notched needle, grooved cannulas, etc. However, the needle can be notched to allow blood flashback to be detected before further insertion of the needle and catheter hub into the vein. Additional details of the various individual components are discussed below with reference to the drawings.

In an example, the housing can embody an elongated U-shaped channel comprising two sidewalls and a bottom wall located therebetween. The walls can form a frame or body of the housing.

An open passage can be provided with the housing that runs generally parallel to the bottom wall. The distal end of the housing can include an enclosed or continuous perimeter without any gap while the remaining part of the housing can embody an open U-shaped channel.

In some example, the distal end can have a gap or a break in one of the surfaces for flexing. The housing can include a pair of mounting holes for fitment with mounting arms or pins of the support piece, slide rails on a top side of the sidewalls, a first interior guide groove, and a second interior guide groove.

The second interior guide groove can be located above the first interior guide groove, elevation-wise, and closer to an upper edge the sidewall. In an example, two guide grooves can be provided on each sidewall.

In exemplary embodiments, a guidewire can be provided to aid in positioning of the catheter tube into a vein. Due to the relatively longer length of the cannula or needle of an extended dwell catheter assembly and the corresponding longer catheter tube required for accessing the deep vein, the guidewire can be provided to prevent or resist flexing of the catheter tube.

A catheter push tag and an integrated catheter push tag, or alternatively referred to as first catheter push tag and a second catheter push tag can be incorporated with the present extended dwell catheter assembly. The combination first and second catheter push tags can be referred to as a catheter activation device, which has the first push tag and the second push tag that can be structured for coupling the two, such as the sidewalls.

The first and second catheter push tags can move together when the first push tag is activated and can move relative to one another when the second push tag is activated. In an example, the first push tag is connected to sidewalls of the housing so that movement of the first push tag in the distal direction also moves the two sidewalls in the distal direction. For example, the wall surface of the first push tag can be integrated with, or unitarily formed with, the walls of the housing so that movement of the first push tag also moves the walls of the housing.

Further, as the second push is mounted to the sidewalls of the housing, such as to guides, tracks or channels of the frame of the housing, movement of the sidewalls by the first push tag also moves the second push tag in the distal direction. Subsequently, as the second push tag is mounted at the respective proximal ends of the two tracks on the two sidewalls, the second push tag can slide along the tracks towards a distal position on the tracks. As further discussed below, this movement of the second push tag allows the catheter hub to separate from the housing.

The catheter push tag can have a head section and a body section that can be integral, such as being singularly or unitarily formed. The head section, which can be arranged at a distal end or portion of the catheter push tag, can include a user interface area with a top surface configured for manipulation of the catheter push tag by the user.

The head section can include a first side surface and second side surface that are connected by the top surface. The head section can additionally include an underside or leg extending from the front wall or front side and having a lip or projection as additionally detailed in FIGS. 4 and 4A as to the structure and functionality of those features. The front side can be provided between the first side surface and the second side surface. The interface between the front side, the first and second side surfaces, and the top surface can be chamfered or rounded with smooth transitions.

A body section can extend from a proximal end of the head section in the proximal direction. The body section is configured to support the integrated catheter push tag and allow the integrated catheter push tag to slide along the length of the body section.

The top surface of the head section can have a surface that is generally planar, that is curved or bow-shape, can have a recess, or can generally be shaped to correspond to or cooperate with a digit of the user.

An interior cavity or space can be provided proximal of the head portion. The interior space can be provided between two sidewalls of the body section, as further described below. The top surface of the head section can optionally incorporate geometric patterning or indicia, which can provide improved grip for the user and/or be for aesthetic purposes. In some embodiments, the geometric patterning can embody recessed strips that are spaced apart or can be formed as cutouts through the wall at the top surface of the head section. In some embodiments, the geometric patterning can be spaced apart protrusions or bumps.

The body section of the housing can comprise two sidewalls extending proximally from the head section. The two sidewalls can include a first side surface and an opposed second side surface. In some embodiments, the two side walls extend separately and generally parallel to one another from the head section towards the proximal end, such as in the proximal direction from the head section.

The two sidewalls can be spaced from one another as they extend in the proximal direction. In some embodiments, a cross bracing structure can connect the two side walls at a position proximal to the head section to provide structural support, such as a brace, for the two sidewalls. If incorporated, the brace can be anywhere along the length of the two sidewalls of the body section, including near the head section or an end opposite the head section or anywhere in between, provided the cross bracing does not interfere with other movable parts or components of the device. Between the two side walls can be the interior cavity or space.

The two sidewalls of the body section can each have a first side surface and an opposed second side surface. The first side surface, which can be referred to as the exterior surface, can extend in the proximal direction away from the head section. The two sidewalls can be a mirror image of one another with minor differences contemplated. Each sidewall can include surface features or contours. In an example, each side wall of the body section can have an upper edge or first edge and a lower edge or second edge and a wall with the wall surface therebetween.

Each sidewall can include surface contouring, such as rails, channels, and/or guides. In an example, the contouring can include intermediary surfaces sized and shaped for fitment with the integrated catheter push tag.

In an example, the intermediary surfaces on each sidewall can embody a recess having a length, or a channel, and the recess can connect to a groove rail, which can have a ledge extending away from the central cavity to provide a structure for the integrated push tag to engage. The shape of each groove rail can resemble a track for engagement by the integrated catheter push tag and can be defined by the recess, by the intermediary surfaces.

The track, which can also be called an upper mating portion, can have a surface inset a predetermined depth from the exterior surface of the sidewall. As such, the upper mating portion can have a smaller thickness relative to the remaining portion of the sidewall structure below the intermediary surfaces.

In alternative embodiments, the wall thickness can be relatively smaller, equal to or bigger than the remaining portion of the sidewall structure, as long size of the track can create a sliding track for integrated catheter push tag. The upper mating portion can further have a groove rail, wherein the groove rail can be inset from the surface of the upper mating surface.

The groove rail can extend along a portion of the length of each side wall. As provided, the groove rail can terminate short of the proximal most end of the sidewall. The proximal end or stop limit of the groove rail can serve as a stop to delimit the proximal travel of the integrated catheter push tag along the two groove rails.

From the position shown in FIG. 2, the integrated or second catheter push tag can be limited from further proximal movement by the stop limit but not distal movement. For example, the integrated catheter push tag can physically abut a structure on the housing to limit further proximal movement. The second catheter push tag can slide or move along the track in the distal direction but can be limited when the front edge of the second catheter push tag abuts the distal stop limit. On the proximal side, the rear edge of the second catheter push tag abuts the proximal stop limit to limit further proximal movement of the second catheter push tag.

The two groove rails on the two sidewalls can provide for fitment with the rail protrusions of the integrated catheter push tag. In some embodiments, each groove rail can be located adjacent to the intermediary surfaces where the groove rail meets with the upper mating portion. Alternatively, the two groove rails and the two rail protrusions on the integrated catheter push tag can be switched so that the integrated catheter push tag incorporates two groove rails and the two sidewalls each incorporates a rail protrusion.

When the rail protrusions are coupled with the groove rails, the integrated catheter push tag is slidable along the length of the groove rails. In this way, when the rail protrusions of the catheter push tag are slidably fitted to the groove rails, the exterior sides of the integrated catheter push tag are generally flush with the exterior sides of the wall structures of the two sidewalls of the catheter push tag. In some examples, the exterior sides can extend further outwardly than the wall surfaces of the sidewalls.

In some embodiments, the side walls can each include a proximal stop limit and a distal stop limit, which can embody physical structures for stopping movement of the integrated catheter push tag in the proximal direction and the distal direction. For example, the stop limits can embody wall structures adjacent the groove rail to provide physical barriers for the rail protrusions on the integrated catheter push tag.

The stop limits can form part of a portion of the body section proximal and distal to the groove rail that do not have the recessing for the intermediary surfaces or the groove rail. The stop limits can prevent proximal and distal sliding movements such that the integrated catheter push tag does not disengage from the catheter push tag. In this way, it can be visualized that the two groove rails are recessed in an intermediary area of the catheter push tag. The stop limits can interface with a first side surface and a second side surface of the integrated catheter push tag.

In use, the first catheter push tag, such as the head, can advance in the distal direction within the housing, which moves the body and the integrated or second catheter push tag mounted to the body in the distal direction. The integrated catheter push tag, such as the body, can then advance in the distal direction along the rails. The first and second catheter push tags therefore can move together as a unit and then the second catheter push tag can move relative to the first catheter push tag in the distal direction.

The first and second catheter push tags, such as the head section and the body of the first and second push tags, are spaced from one another a first distance when the first catheter push tag moves in the distal direction. The distance between the first and second catheter push tags is narrowed and the first distance reduced when the second catheter push tag moves relative to the first catheter push tag in the distal direction, which can go to zero when the second catheter push tag touches and proximal edge of the first catheter push tag.

The integrated catheter push tag can have a generally U shape structure or body when viewed from an end view or from an end cross-section and can comprise a first side surface, a top surface, and a second side surface. The top surface can couple to the first side surface and the second side surface through chamfered or radiused surface portions. The first side surface and the second side surface integrated catheter push tag can extend at least a portion of the length of the integrated catheter push tag and the radiused portion can extend the length of the integrated catheter push tag.

At a bottom side of the first side surface and the second side surface can be the rail protrusions extending inwardly to engage the groove rail of the body section. The rail protrusions can extend along the length of the first side surface and the second side surface. In some embodiments, the rail protrusions extend only along a portion of the length of the first side surface and the second side surface.

The rail protrusions can extend inwardly from the first and second side surfaces to engage the respective groove rails on the two sidewalls. The proximal end of the integrated catheter push tag can extend further proximally than the end edge of the two sidewalls.

The top surface of the integrated catheter push tag can be shaped to cooperate with a digit of the user. The top surface can have geometric patterning, which can provide improved grip for the user or be for aesthetic purposes. In some embodiments, the geometric patterning can be recessed cutouts. In some embodiments, the geometric patterning can be protrusions or bumps. Curved or recessed surfaces can optionally be incorporated to improve gripping between the top surface and a user's finger.

The catheter push tag can further include distal guides projecting from the body section. In an example, one distal guide projects distally from a distal portion of each sidewall. The two distal guides can aid in lateral stabilization and guidance of the catheter push tag in the housing when the user manipulates the head section. Each distal guide can have a generally square or rectangular cross-section.

The two distal guides can be inset from the exterior surfaces of the side walls to allow for a clearance for ready sliding and can extend distally short of the front side or front wall. Each distal guide can have an arcuate or curved proximal end to from a smooth contour with the curved section of the side wall.

The body section of the catheter push tag can further include exterior guide protrusions. In an example, one exterior guide protrusion projects radially outwardly from each of the sidewalls away from the cavity or space of the body section. Each exterior guide protrusion can protrude outwardly from the side wall and can extend substantially along the length of the sidewall, near or adjacent the lower edge.

In an example, each exterior guide protrusion can extend radially relative to the lengthwise axis of the body section from a first end of the sidewall to a second end of the sidewall. In other examples, the exterior guide protrusion extends from a position proximal of the distal guide to a position substantially co-planar with the end edge of the sidewall. In other examples, the exterior guide protrusion can embody two or more sections that can extend up to or short of the end edge.

Each exterior guide protrusion can extend orthogonally from a sidewall. The exterior guide protrusions can be sized and shaped to correspond to the two first interior guide grooves of the housing. In an example, the exterior guide protrusions can be configured for sliding engagement with the two lower first interior guide grooves of the housing, as further discussed below.

A guidewire push tag provided herein can have a generally U shape structure or body from an end view comprising a first side surface, a top surface, and a second side surface. The top surface can be shaped to correspond to or cooperate with a digit of the user. The top surface can have geometric patterning, which can provide improved grip for the user or be for aesthetic purposes. In some embodiments, the geometric patterning can be recessed cutouts. In some embodiments, the geometric patterning can be protrusions or bumps. The side surfaces can have surface features and non-uniform edges.

The first side surface and the second side surface of the body of the guidewire push tag can be coupled to the top surface at upper edges. In an example, the first and second side surfaces are unitarily formed with the top surface, such as by injection molding. A bracket can be positioned proximally of the guidewire push tag. More particularly, the bracket has a first arm located to one of the side surfaces of the guidewire push tag. As shown, the bracket is coupled to the elongated extension and extends from the second side surface with extension from the first side surface being optional.

In an example, an elongated extension extends from a proximal edge of the second side surface. The elongated extension can have a generally square cross-section and can have a length that is about 50% to 150% of the length of the second side surface. However, the length of the elongated extension is not limited to the disclosed range and can vary, such as being longer than 150% of the length of the second side surface.

The polygonal shaped cross-section can include a first side edge. The bracket can be secured to the first side edge of the elongated extension, as shown in FIG. 3. In an example, the bracket is bonded or glued to the elongated extension, such as to the first side edge of the elongated extension. In an alternative embodiment, the bracket can be connected differently, such as by tight fitting to the elongated extension or be connected to the inner side of the elongated extension.

In an example, the first and second side surfaces of the body of the guidewire push tag each comprises a distal end or portion that is irregular, undulating, and/or includes contoured portions. In an example, the distal portion is other than a square or straight edge corner. The distal portion at each side surface can include a cut out so that portions of the guidewire push tag can be located within the interior of the housing while other portions of the guidewire push tag can locate above the housing and rest on the two slide rails of the housing.

Along each of the two bottom edges of the first side surface and the second side surface, there can be an exterior guide protrusion protruding outwardly away from a central portion or cavity of the guidewire push tag. The two exterior guide protrusions can ride against the underside of the two slide rails, opposite the rest wings. In an example, the guidewire push tag can have a rest wing projecting generally perpendicular from the first side surface and from the second side surface. As shown, the two rest wings are located generally closer to a distal end or distal portion of the guidewire push tag. Each rest wing can have a curved or contoured edge to match the shaped distal portion of the housing.

The exterior guide protrusions can extend along a portion or the entire length of each of the first side surface and the second side surface of the body of the guidewire push tag. The exterior guide protrusions can be located at a bottom edge of the first side surface and the second side surface when assembled. The exterior guide protrusions can be sized and shaped to correspond to the second interior guide groove of the housing.

Two actuation bars can be provided with the guidewire push tag.

In an example, the two actuation bars can be located adjacent the two side surfaces. In a particular example, the two actuation bars can be formed with the guidewire push tag, such as being unitarily formed in a plastic injection molding process.

With reference to FIG. 5, which shows the assembly without the U-shaped body, the two actuation bars can be configured to interact with the two rotation stops on the support piece, such as compressing them together, to release the support piece from the restriction imposed by the limiting walls. This then allows the support piece to rotate about the axis defined by the mounting arms to rotate the central body away from the path of the catheter hub to enable separation of the catheter hub from the housing. The actuation bars and/or the rotation stops on the support piece can have tapered surfaces to allow engagement so that the actuation bars can compress the two rotation stops therebetween to free the support piece from the constraint of the housing, as further discussed below.

Extending in a rearward, proximal direction from the body of the guidewire push tag, can be a mounting portion or elongated extension. The mounting portion can extend from a bottom edge of one of the first side surface and the second side surface. In an exemplary embodiment, the mounting portion can extend from a bottom edge of the second side surface. The mounting portion can be rectangular in shape and have a rectangular or polygonal cross section as it extends in the proximal direction from the guidewire push tag.

The bracket can have a first arm with a mounting portion at a first end and a hook section or portion at an opposed, second end. The first arm and the hook section or portion can define a J-shape structure when viewed from above. The first arm can be generally uniform as it extends from the distal end to the proximal end just before transitioning to the hook section.

In some examples, the first arm can have a cross shape or T-shape cross section. The mounting portion can correspond to the mounting portion of the guidewire push tag. In some examples, the mounting portion extending from the guidewire push tag and the mounting portion can include a tongue and a groove combination, detents, pin and hole, or other mechanical means to facilitate coupling the two together. In other examples, the two can be bonded or welded together. Optionally, the two components can be co-molded or insert molded together.

The hook section can extend from the first arm and can be unitarily formed therewith. The hook section and the first arm can both have upper or tip surfaces that are co-planar or one can be recessed from the other and can be parallel to one another. The hook section can alternatively be coupled to the first arm, such as by detents with optional adhesive. The hook section can have a proximal end or edge and a distal end or edge.

The proximal edge can be smooth or have a flat end surface while the distal end can have a tapered shape that narrows in cross section at a central portion with an apex and widens at portions coupling to the first arm and the second arm. The second arm is located on the opposite end of the hook section from the first arm.

In some examples, the elongated extension and the bracket can be eliminated and the guidewire can be attached directly to the body of the guidewire push tag. For example, where the elongated extension and the first arm are provided, a metal wire length can connect to the body of the guidewire push tag. The metal wire length can be sized with a gauge that does not readily flex or bend. Where the holding section is currently provided, a U-shape bent can be provided with the metal wire length. A contoured section can be provided with the U-shape bent to align to a guidewire length, which can be welded or coupled to the metal wire length using a mechanical coupling. A guidewire can thus be provided with the bracket but by using a sufficiently heavy metal wire extending from the guidewire push tag.

The second arm can have an angled portion that angles downwardly, elevation-wise, to offset a guidewire holder from a plane formed by the first arm and the hook section. In some embodiments, the angled portion of the second arm can be a smoothly curved portion to offset the guidewire holder. Alternatively, the second arm can have a sharp angular portion to generate the planar offset. In yet other examples, the guidewire holder can extend from a vertical drop or a bar that extends from the second arm.

The offset provided by the angled portion can change the position of the guidewire holder, elevation-wise, so that the guidewire attached thereto can align with the catheter tube of the needle assembly following assembly of bracket. The guidewire holder can have a rectangular base coupled to the second arm, wherein the rectangular base flares out, such as having a wider body, from the second arm to create an enlarged cross-sectional shape.

The rectangular base can have a guidewire hub extending therefrom, which can be unitarily formed with the rectangular base. A recess or hole can be provided with the guidewire hub to hold the guidewire, optionally with adhesive. In an assembled state, the guidewire can extend in a parallel direction to the first arm.

When the guidewire push tag and the bracket are assembled as an integral unit, they can take on a C shape with the push tag and the hook section serving as end pieces of the C, when viewed from above. In assembled state, the guidewire can extend in the distal direction between the first side surface and the second side surface of the guidewire push tag. In exemplary embodiments, the guidewire push tag and the bracket can be sized and shaped so that the guidewire passes down a middle section between the two side surfaces.

During use, distal movement of the body of the guidewire push tag can move the bracket attached to the body distally forward, which also moves the hook portion and the guidewire hub in the distal direction. As the guidewire is attached to the guidewire hub, the guidewire is moved distally by distal movement of the guidewire push tag.

Further, distal movement of guidewire push tag moves the two actuation bars in the distal direction. With further reference to FIG. 5, shown without the body of the guidewire push tag, the two actuation bars can be configured to move distally by the guidewire push tag to interact with the rotation stops to move the two side arms of the support piece inwardly closer together to allow the support piece to free itself from the constraint of the limiting walls.

FIG. 4 illustrates a cross-sectional view of an exemplary embodiment of a catheter hub with exterior threads at a proximal end, the catheter push tag, and the integrated catheter push tag in an assembled, un-activated state. The catheter hub can be generally understood as having a conical or cylindrical shape with a body having a female Luer taper at the proximal open end, as would be understood by one of ordinary skill in the art.

The catheter hub can include a safety shield or needle guard disposed in an interior of the catheter hub. The safety shield can be provided to guard the tip of the cannula or needle when the cannula is separated from the catheter hub following successful placement of the catheter tube into the patient.

On withdrawal of the hollow needle from the catheter hub following successful venipuncture, a change in profile provided near the needle tip and having the form of a radial projection on the hollow needle, such as by crimping, engages the safety shield, such as the opening on the proximal wall of the safety shield, so that the safety shield can be removed from the catheter hub with the needle.

An exemplary safety shield can have two arms arranged on either side of a median plane defined by the needle shaft in an un-activated state. When the needle is retracted through the catheter tube during separation, the needle tip can move proximal of the two distal walls of the two arms, allowing the two arms to move, such as spring or deflect radially to cover the needle tip to prevent unintended needle sticks. In other examples, the change in profile can include a sleeve, a notch, or a material buildup on the shaft of the needle. In yet other examples, the needle guard can have a single arm or two arms that extend along the length of the shaft without crossing the needle axis.

In embodiments, when the needle is removed from the catheter hub, the safety shield can be held generally stationary until the change in profile, such as a crimp, near the needle tip comes to abut on a rear proximal wall of the needle guard and the needle tip moves proximally of the two distal walls on the safety shield. At this point, the two spring arms, which are no longer biased outwardly in the radial direction by the needle, can spring inwards to cover the needle tip, whereupon the safety shield with the needle can be removed from the catheter hub.

The needle guard or safety shield can be made of thin metal sheet being stamped into the desired shape and then cold work or formed, such as bent, into final shape wherein, in the biased position, one or two elbows of the safety shield engage or engages the catheter hub and in the unbiased position the safety shield disengages from the catheter hub and move radially to a smaller radially profile so that the needle guard can pass through a small internal diameter section of the catheter hub.

The catheter hub can include a retaining tab or push tab projecting perpendicularly or radially outwardly from the outside surface of the catheter hub. The retaining tab can be generally rectangular in shape with other shapes contemplated and can be used as a leverage point of structure. For example, the leg on the first catheter push tag can push against the push tab to advance the catheter hub in the distal direction.

An exemplary catheter push tag can include an underside or leg having a retaining portion extending from the head section, which has the top surface with geometric patterning. The bent back leg from the front side can act like a leaf spring and form part of a leverage with the retaining portion. The retaining portion can be at an end of the bent back leg. The bent back leg can be angled and can deflect by moving upwardly towards the top surface of the head portion of the catheter push tag.

The bent back leg can be made of a material that allows for elastic deformation. In the un-activated assembled state, the bent back leg can position the retaining portion such that it can act on the retaining tab or push tab of the catheter hub to retain the catheter hub and prevent the catheter hub from accidental separation from the assembly.

The retaining portion can exert force in a direction along the axis of the catheter hub. For example, when moving the catheter push tag in the distal direction during use, the retaining portion can push the push tab in the distal direction to then advance the catheter hub and the catheter tube in the distal direction. Advancing the catheter push tag can also move the body section of the frame of the housing.

As the integrated catheter push tag can be mounted to the body section and the integrated catheter push can have a pushing leg incorporated therewith, movement of the catheter push tag in the distal direction can also cause the push end of the pushing leg to push the catheter hub in the distal direction. As further discussed below, the catheter push tag can be pushed distally after initial catheterization with the needle and following advancement of the guidewire push tag to advance the guidewire into the vein to facilitate guiding the catheter tube.

In an alternative arrangement, the retaining portion can be located distally of the push tab. Thus, movement of the catheter push tag in the distal direction also moves the catheter hub in the distal direction via the push end of the push leg pushing on the catheter hub as described above. An advantage of locating the retaining portion distally of the push tab is that it provides a user with the option to move the catheter push tag in the proximal direction to cause the retaining portion to push the push tab in the proximal direction to move the catheter hub in the proximal direction.

The integrated catheter push tag can be slidably mounted to the catheter push tag, which has a body section. Thus, the integrated catheter push tag can slide with the body section, such as when located at a proximal position of the body and the catheter push tag is advanced in the distal direction, and can slide relative to the body section by placing a finger on the body of the integrated catheter push tag and advancing the body relative to the head section and the catheter push tag, as further discussed below.

The integrated catheter push tag can have a top surface. The integrated catheter push tag can include a push leg. The push leg can extend from a distal end of the top surface.

The push leg can have a curved portion and a pushing portion or push end. The curved portion can be sized and shaped to extend downwardly, elevation-wise, from the body of the integrated push tag and can have a width that fits within the width of the cavity between the two sidewalls of the body section.

The pushing portion or push end can be aligned to contact or abut a proximal end of the catheter hub. The pushing portion can exert a force on the catheter hub in a distal direction along the axis of the catheter hub to advance the catheter hub in the distal direction. For example, when the integrated catheter push tag is advanced in the distal direction after the first catheter push tag advances the catheter hub in the distal direction, the pushing portion or push end is also advanced to then push the catheter hub in the distal direction. When pushed by the integrated catheter push tag, the push tab moves distally and separates from the retaining portion of the bent back leg.

The housing can have mounting holes for receiving the pins of the support piece. One mounting hole can be provided on each sidewall of the housing.

The support piece can be optional but preferred for steadying or supporting the needle and the catheter tube to prevent or limit flexing of the needle and catheter tube during at least part of the advancement of the guidewire. In the assembled state, the support piece can have the mounting pins inserted in the mounting holes. The support piece can have a generally W shape body, the W shape body defined by two side arms and a central body piece. In an example, the two side arms can each generally be rectilinear in configuration and each can have at least two spaced apart side edges.

The two side arms can each be spaced from the central body piece by a gap and connect to the central body piece along lower joining sections, near a cutout. The central body piece can have a blunt tapered tip, which can define enlarged gaps between the central body piece and the two side arms at the tapered tip end of the central body piece. These enlarged gaps can provide added clearance for the two side arms to compress or move into during assembly of the mounting pins into the mounting holes and during deflection of the two side arms when activating the support piece by the actuation bars on the guidewire push tag to allow rotation of the support piece away from the path of the catheter hub to permit distal movement of the catheter hub out the distal end of the housing.

The mounting pins can attach to the two side arms and then project outwardly to define a rotational axis. The pins can be generally round. The mounting pins can further include rotation stops projecting radially outward from the mounting pins, one on each mounting pin. Each rotation stop can extend perpendicularly from the axis defined by the corresponding mounting pins. As shown, the rotation stop can include a ramp surface so that the two ramp surfaces of the two rotation stops can be pressed together by the actuation bars located on the guidewire push tag. In an example, the support piece can be made from a plastic material with options to produce the support piece from other materials, including from metal. The support piece can be unitarily formed as a single unit or can be assembled from multiple components.

The central body piece of the support piece can include a radiused cutout corresponding to the catheter tube. In an example, the cut out has a width that is about the same size as the diameter of the catheter tube or can be slightly larger, such as by 0.5 thousandths to about 5 thousandths larger. However, the dimensions are not limited and can have other working ranges. As shown, the curved central portion of the cutout is configured to contact the catheter tube to help guide the catheter tube and the needle located therein between the housing lower surface and the cutout during cannulation.

In some examples, the housing lower surface can include a pre-formed shape to facilitate guiding the catheter tube. For example, a channel having an arc shape can be provided on the housing lower surface to help guide the catheter tube and the needle located therein.

The radiused cutout can contact and support the catheter tube and the needle located therein to lessen deflection of the catheter tube and the needle inside the catheter tube during insertion into a patient and during advancement of the guidewire. Thus, the catheter tube and the needle inside the catheter tube can be supported between the support piece and the housing bottom surface to limit or prevent the catheter tube and the needle from kinking and/or flexing during advancement of the needle and catheter tube following initial catheterization and verification of proper vein placement and advancement of the guidewire. The angle between central body piece and the rotation stops can be obtuse. The support piece releases upon advancement of the guide wire.

In an example, the two side arms can define a width and the width of the two side arms can be larger than the width or gap defined by the two limiting walls on the nose section of the housing. The differences in dimensions forces the support piece to remain angled as due to the two limiting walls restricting movement of the two side arms, to provide support between the support piece, and in particular the cutout, and the housing lower surface to support the needle.

The support piece can be activated to rotate about the axis defined by the two mounting pins to then allow the catheter hub to advance distally of the support piece. For example, the two side arms can be forced to squeeze through the gap defined by the two limiting walls, such as by deflecting two arms together, to then allow rotation. In an example, the guidewire push tag can be provided with a pair of actuation bars. When the guidewire push tag is advanced in the distal direction to advance the guidewire, the pair of actuation bars formed with the guidewire push tag can squeeze the two rotation stops inwardly together and inwardly relative to the lengthwise axis of the housing. This can force the two side arms together to free the support piece from the constraint of the two limiting walls to then allow the support piece to rotate about the mounting arms. Distal advancement of the catheter hub provides the rotational force for rotating the support piece.

The housing can incorporate a retention block. The retention block can be located at an intermediary position along an interior of the housing. The retention block can be a raised feature in the interior of the housing, protruding from a bottom interior surface of the housing. In some embodiments, the retention block can be generally rectangular, protruding from the bottom interior surface. The retention block can include a central through opening extending along the proximal to distal direction of the housing. In embodiments, the needle can be fixed to the retention block by mechanical means, by adhesive, or both.

The retention block can provide for at least one of retention of the needle and as a movement limiter for the guidewire. In embodiments, the guidewire holder is located on a proximal side of the retention block when the needle assembly is assembled. The guidewire can pass through the opening and through the lumen of the needle towards a distal end of the assembly. Accordingly, when the bracket is moved by manipulation of the guidewire push tag, the bracket can be limited in its maximum travel when the guidewire holder contacts the proximal side of the retention block.

The retention block can include a top surface, which can be sized and shaped to allow movement of the push leg on the integrated catheter push tag past the retention block or act as a guide against deflection of the push leg.

In an assembled state, the components of the assembly are coupled with the housing. Accordingly, in the assembled state, the guidewire push tag, the catheter push tag, and the integrated catheter push tag can all slidably couple to the housing. Additionally, the back cover can cover at least one of the push tags to prevent accidental, false activation, of the covered push tag(s). In some examples, the cover can be omitted or can be singularly formed with the housing. The push tags can be said to be stacked in that, in the assembled state, the integrated catheter push tag can be covered by the cover and only the guidewire push tag is shown.

The guidewire push tag can normally overly the catheter push tag in the ready to use position of the device. When the catheter push tag is then moved in the distal direction after movement of the guidewire push tag, the movement of the catheter push tag can move the integrated catheter push tag in the distal direction due to the stacking of the integrated catheter push tag to the body section of the catheter push tag.

The rest wings can be slidably rested on the slide rails of the housing. The radiused cutout of the support piece can contact and support the needle inside the catheter tube during initial cannulation into a patient. The guidewire push tag can advance to a distal position, which can be the position after the guidewire is advanced following initial cannulation of the needle.

The device of the present embodiment can be used by first performing cannulation of the needle, following by advancing the guidewire and then advancing the catheter tube over the guidewire and using the guidewire to guide the catheter tube. In the pre-activated position, the guidewire push tag can be located proximally adjacent to the distal edge of the back cover and/or overlies the catheter push tag.

The various push tags 350, 400, 500 can be stacked in an un-activated state to prevent accidental, false activation, of the push tag that is or has been covered. By having sequential stacking and uncovering of the next push tag through manipulation of the immediate prior push tag, the user can be prevented from accidently manipulating the push tags out of sequence.

In an example, the guidewire push tag can overly the catheter push tag or is superjacent the catheter push tag in the first position, or ready to use position of the assembly, and the back cover can cover the integrated catheter push tag in a stacking arrangement.

As stacked or arranged, only the guidewire push tag or first push tag is exposed and can be accessed and moved by a user in the ready to use position. Thus, the user cannot manipulate any other push tag aside from moving or manipulating the only exposed first push tag. The catheter push tag, such as the top surface of the head section of the catheter push tag, can be accessed and moved after the guidewire push tag is distally moved and the integrated catheter push tag can only move after the catheter push tag is distally moved, as further discussed below.

In the first, un-activated state, all of the push tags can be positioned in their rearmost or respective proximal positions. The guidewire push tag can be positioned adjacent to the back cover but not covered by the back cover. In this position, the bracket is in a rearward position near the proximal end of the assembly. As shown, the guidewire can go through the opening of the retention block and the needle, and the proximal edge of the guidewire push tag contacts the distal edge of the cover with a gap between the two contemplated.

In an example, the top surface of the guidewire push tag can be generally flushed with the top surface of the back cover. A light gap can be provided near the inside surface of the guidewire push tag and the top surface of the head section of the catheter push tag to avoid interference so that movement of the guidewire push tag does not inadvertently also move the catheter push tag.

Located underneath the guidewire push tag can be the catheter push tag and the catheter hub, which can be said to be located subjacent the guidewire push tag. In this state, the catheter tube and the needle can extend past the support piece and extend distally of the nose section of the housing. The needle tip can extend beyond the distal opening of the catheter tube for cannulation. Rearward or proximally of the guidewire push tag and the catheter push tag, the integrated catheter push tag can be covered by the back cover. Accordingly, the only push tag that is readily accessible to a user in this initial state is that of the guidewire push tag.

A practitioner can initiate cannulation using the needle device in the initial state using only one hand while holding and using a visualization or vascular probe, such as a handheld Doppler ultrasound machine, with the other hand. Once initial placement of the needle tip is made and blood flash back is confirmed, the user can initiate the next step.

After the guidewire push tag has been manipulated, such that it has been slidably actuated towards the distal direction, the guidewire push tag is slidably moved to a position nearer the distal end of the housing. As such, the bracket coupled to the guidewire push tag can similarly move by the guidewire push tag so that the guidewire holder can contact the retention block to limit further travel. Due to this movement, the guidewire is also advanced further distally. In other examples, the body of the guidewire push tag abuts a surface or structure of the housing to limit further distal advancement of the guidewire push tag, and hence the guidewire holder.

The guidewire can be used in this case to aid in guidance of the catheter tube and also to prevent double puncture of the vein, especially for relatively longer catheter tube.

In the second state, the distal direction movement of the guidewire push tag can now expose the catheter push tag, which can couple to the catheter hub, the body section and the integrated catheter push tag, which can have a push leg with a pushing end for pushing the proximal end of the catheter hub. Accordingly, the catheter push tag can now be accessible for manipulation, such as to grip by a user and advanced in the distal direction. However, the integrated catheter push tag can still be covered by the back cover in this second state as the catheter push tag has not yet been activated, such as being moved in the distal direction.

A third state can be where the catheter push tag has been manipulated such that it has been slidably actuated towards the distal direction, which initially moves the catheter hub via the push leg of the integrated catheter push tag, which can connect to the catheter push tag. Between the position of the catheter push tag shown in FIG. 9 and in FIG. 10, the catheter push tag can first be pushed by a user in the distal direction to just before the catheter push tag slides under the guidewire push tag, which can then expose the integrated catheter push tag from the cover. The user can then move his or her grip from the catheter push tag over to the integrated catheter push tag to advance the integrated catheter push tag further distally.

In one example, the catheter push tag remains exposed just proximal of the guidewire push tag following advancement of the catheter push tag by the user or practitioner. But when the integrated catheter push tag is advanced distally after being exposed from the cover by distal movement of the catheter push tag, the body of the integrated catheter push tag moves independently relatively to the catheter push tag about the rails or tracks of the body section until the two push tags contact, at which point further advancement of the integrated catheter push tag pushes both bodies distally.

In other example, the catheter push tag is moved to its distal position by first moving the head section to advance the catheter push tag. When further movement is obstructed by the guidewire push tag, the user can push on the proximal edge or end of the head section of the catheter push tag to continue to advance the head section under the guidewire push tag. Then when the device is in the position shown in FIG. 10, the user can adjust his or her grip onto the integrated catheter push tag to advance the integrated catheter push tag.

In the third state, the catheter hub is still located within the housing but has started to be released, with the nose section of the catheter hub being exposed distally of the housing and distally of the support piece. As the catheter push tag moves distally, the back bent leg extending from the catheter push tag can compress against the top surface of the housing. The compression of the back bent leg can bias the retaining portion upward and allows for the retaining portion to clear the push tab on the catheter hub. At the same or about the same time, the support piece, which was previously activated and rotated about the axis defined by the two mounting pins when the guidewire push tag is advanced, can provide clearance or space for the catheter hub to move distally of the support piece.

The extended dwell catheter assembly of the present invention can have a fourth state. The fourth state can be a state where the integrated catheter push tag has been manipulated such that it has been slidably actuated towards the distal direction. In so doing, the push leg, and more particularly the pushing end of the push leg, depending from the integrated catheter push tag can push the proximal end of the catheter hub in the distal direction. As the catheter hub can now clear the retaining portion connected to the catheter push tag when moving in the axial direction, the integrated catheter push tag can push the catheter hub distally away from the housing to separate from the housing.

The extended dwell catheter assembly of the present invention can have a fifth state. The fifth state can be a state where the catheter hub is separated from the rest of the assembly. As the housing and the various components assembled thereto increasingly separate from the catheter hub, the needle and the guidewire can withdraw from the proximal end of the catheter hub. As the needle moves proximally to separate from the catheter hub, a change in profile provided near the needle tip, such as a radial projection on the hollow needle, a crimp, or a material buildup, can engage the safety shield, such as an opening on a proximal wall of the safety shield, to retract the safety shield from the catheter hub with the needle.

In an example, only the catheter hub and catheter tube are left in place with the patient when the needle and the guidewire are removed. Optionally, a valve and a valve opener can be provided with the catheter hub to stop fluid flow to or from the catheter hub, such as to stop blood flashback to enable coupling of an infusion line to the catheter hub.

In an alternative embodiment, the support piece can have a central portion with biasing, resilient, or springing properties as part of the central body. The support piece can have a folded over body piece and two side arms that are attached to the central body by two connecting or joining portions. The present support piece can be used in a similar manner as other support pieces described elsewhere herein and usable with the midline catheter assembly disclosed herein.

The central body portion can be defined by a continuous portion of material that is bent and shaped to provide spring like characteristics. From each side arm, the support piece can have a joining section connected to the body portion. The body portion can have an overlapping first body portion that overlaps with a second body portion, which has a split or seam therebetween that can separate or deflect upon advancement of the guidewire push tag, which can incorporate actuations bars to press the two rotation stops on the two mounting pins inwardly to facilitate separation at the seam.

With the first and second body portions deflected and separated by the guidewire push tag, subsequent advancement of the catheter hub can further deflect the support piece to further open up to allow the catheter hub to pass therethrough. A cut-out can be provided on each of the first body portion and the second body portion to reduce rigidity to the two body portions to allow them to more readily deflect when pushed by the catheter hub.

The first body portion and the second body portion can be joined by a folded over flap. The folded over flap can have a cut-out to define two bent sections. The first and the second body portions can be provided with a guide passage and guiding edges. The folded over flap can have a support edge.

The catheter tube and needle can pass through the guide passage and be supported by the support edge on the folded over flap and the two guiding edges, which can limit or help prevent kinking.

The catheter tube can be inserted through the guide passage. As the first body portion is separated from the second body portion except at the two bent sections that join the folded over flap, the relationship between the first and second body portions can be used to apply a biasing force against the catheter tube and to deflect when pushed by the catheter hub.

In an alternative embodiment, the support piece has a passive release front gate and can couple to the housing of the extended dwell catheter assembly, which can be similar to the dwell catheter assemblies discussed elsewhere.

A pair of gates 700, 720 can be provided for supporting the needle 108 and the catheter tube 104 during cannulation. The two gates can be generally symmetrical across a centerline of the assembly.

The pair of gates rotate around respective pivot points that are spaced from the centerline of the assembly, generally coaxial with the length of the needle. Each of the gates can have a substantially L shape with a base portion and an extended portion forming the L shape. Each of the gates can have a cylindrical portion with a boss surrounding the pivot point, such that the boss can be concentric with the pivot point. Extending in a radial direction from the cylindrical portion, a radially outward projection arm, forming part of the base, can be coupled with a gate portion, which forms part of the extended portion of the generally L shape structure. Substantially perpendicular to the projection arm, there can be a rotation stop that projects in the radial direction from the surface of the cylindrical portion offset from the center point or pivot point.

The projection arm can have a substantially rectangular cross section as it extends in the radial direction from the cylindrical portion. The gate portion can have a larger cross-sectional area than the projection arm when viewed perpendicular to the centerline of the assembly.

It is envisioned that the gate portion of each of the pair of gates can have an opening or recess sized to fit the catheter tube. As shown, each gate portion can have a shape of a half or partial hollow cylinder.

When the catheter hub is desired to be released, the distal tip of the needle hub can act on the gate portions of the pair of gates, which can previously be released by advancing the guidewire push tag to press against the two rotational stops to allow the two gate portions to partially open. The pair of gates can then rotate outwardly further to unblock the path for the catheter hub to allow separation of the catheter hub from the rest of the assembly. In an example, the pair of gates rotate freely following activation by the guidewire push tag, which is advanced before the catheter push tag.

An alternative extended dwell catheter assembly can include a housing, a catheter hub, a catheter tube, a pin head, a guidewire push tag, and a catheter push tag.

The housing can have a main section and a distal section. The main section can be substantially rectangular in shape. The distal section can extend from a connecting side wall of a distal end of the main section. The distal section does not continuously extend from at least one adjacent side wall to the connecting side wall, thereby defining a gap between the distal section and the main section. The distal section can be narrower in width than the main section. The distal section can also be substantially rectangular.

A guidewire can be advanced by manipulation of the guidewire push tag on the top of the main section of the housing. The housing can additionally have a retention block for the guidewire. The catheter hub can be guided by the pin head. When the catheter push tag is manipulated forward to the distal end, the movement can allow for the catheter to disengage from the pin head from the bottom of the assembly.

An alternative guidewire push tag can have a distal narrow portion attached to a narrow distal arm. The distal arm can taper into a main body section, which can itself couple with a proximal end with two opposed extrusions.

In a position where the guidewire is extended, the guidewire push tag can overlap with the pin head.

Methods of making and of using extended dwell catheter assemblies and their components as described herein are within the scope of the present invention.

BRIEF DESCRIPTION OF THE DRAWINGS

These and other features and advantages of the present devices, systems, and methods will become appreciated as the same becomes better understood with reference to the specification, claims and appended drawings wherein:

FIG. 5 shows a cross-sectional view of an exemplary embodiment of the housing taken along a horizontal plane cutting through the mounting hole.

FIG. 6 shows a perspective view of the housing.

FIG. 7 shows a perspective view of an exemplary embodiment of an extended dwell catheter assembly 100 in an assembled state.

FIG. 18 shows an un-activated, assembled, exemplary embodiment of the catheter assembly.

FIG. 20 shows a perspective view from the bottom of the assembly.

DETAILED DESCRIPTION

Figure 1:
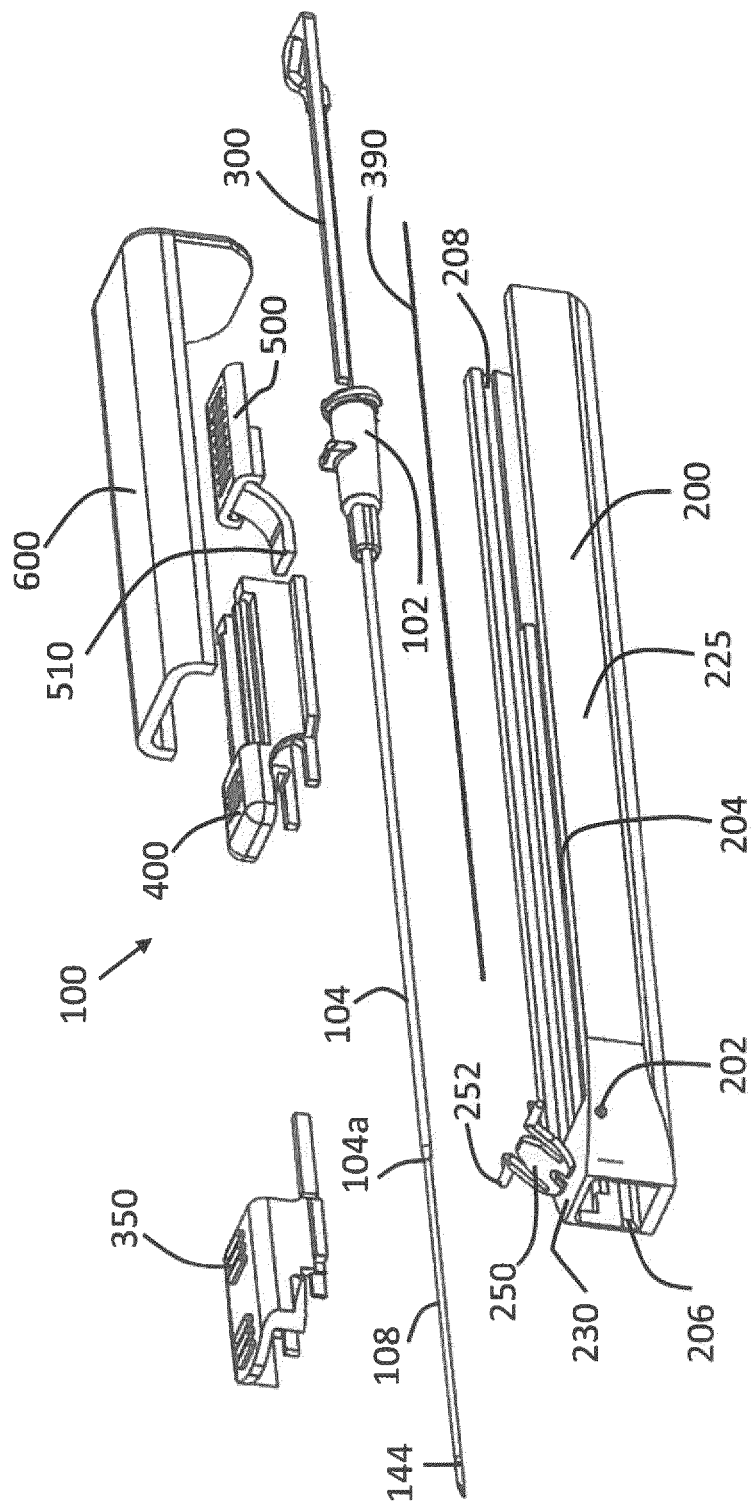
FIG. 1 shows an exploded view of an exemplary embodiment of an extended dwell catheter assembly.

The detailed description set forth below in connection with the appended drawings is intended as a description of the presently preferred embodiments of extended dwell catheters and catheter assemblies provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Generally, when a physician has a difficult time inserting an intravenous catheter to gain peripheral circulation of a patient, the physician can resort to accessing a deep vein. In order to access a deep vein, the physician can use a visualization tool, such as an ultrasound, to guide catheterization with a catheter coupled to a deployment device. After localization of the deep vein with the visualization tool for cannulation by a needle, the physician can then manipulate the catheter and the deployment device with both hands in order to position the catheter as well as to separate the catheter from the needle and the deployment device. In such a deployment device, a catheter hub is attached to additional components of the deployment device, which is required to be removed after placement of the catheter tube into the vein, such as the peripheral veins of an upper arm.

The present disclosure includes an extended dwell catheter assembly that can generally allow for one-handed operation by a physician when attempting to gain intravenous access so that the physician may operate a visualization tool with the other hand throughout the catheterization process. In doing so, the continued visualization of the catheterization process can provide for improved accuracy and limit the need for shifting between cannulation and catheterization.

While the deployment device in accordance with aspects of the invention can incorporate multiple moving parts, movements of said parts can be controlled or sequenced in a manner that leads to proper or accurate deployment of the parts, in the sequence intended or desired. Thus, the present disclosure can provide a safeguard against false activation of the catheter before movement of the needle or guidewire, as examples, by the physician or user by having stacking or overlapping push tags to control the sequence of how the various parts are deployed.

The devices and methods of the present disclosure can increase first stick success through a one-handed technique and can provide an intuitive design, which requires minimal training for physicians. The one-handed technique provides the option for a physician or user to simultaneously perform the catheterization process with one hand while using a visualization tool, such as an ultrasound, with the other hand. Alternatively, the user of the device can rely on a second user to operate the visualization tool while the first user operates the catheter of the present disclosure.

With reference now to FIG. 1, an exploded view of an exemplary embodiment of an extended dwell catheter assembly 100 is shown. The extended dwell catheter assembly 100, or catheter assembly or assembly for short, can include a catheter hub 102, a cannula or needle 108, a catheter tube 104, a housing 200, a support piece 250, a bracket 300, a guidewire push tag 350, a guidewire 390, a catheter push tag 400, an integrated catheter push tag 500, and a back cover 600. The catheter push tag 400 can be referred to as a first catheter push tag and the integrated catheter push tag 500 can be referred to as a second catheter push tag.

Figure 8:
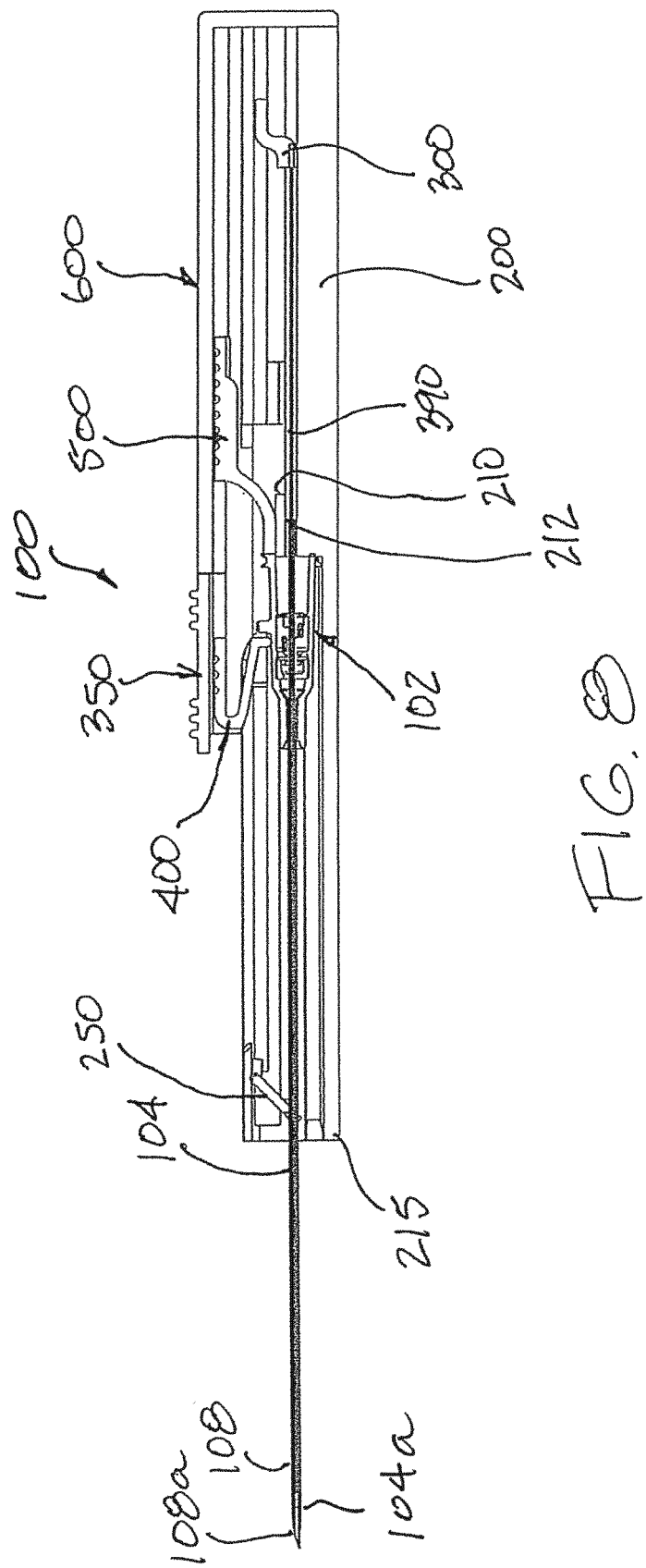
FIG. 8 shows a first, un-activated state of the catheter assembly.

For reference and visualization purposes and when the various components are assembled as shown in FIG. 8 and generally visualized in the exploded view of FIG. 1, the side of the housing 200 with the support piece 250 can be understood as a distal direction or distal end and the side of the housing 200 with the back cover 600 can be understood as a proximal direction or proximal end. The distal direction of the cannula can also be viewed as the direction towards the tip of the cannula and the proximal direction is the opposite direction. In this way, the farthest end tip of the cannula opposite the catheter hub 102 can be understood as a distal end or direction.

The back cover 600 can be understood as a top side or top end of the catheter assembly 100. The cannula 108 of the present disclosure can be with or without flashback features, such as a notched needle, grooved cannulas, etc. However, the needle 108 can be notched to allow blood flashback to be detected before further insertion of the needle and catheter hub into the vein. Additional details of the various individual components are discussed below with reference to the drawings.

In an example, the housing 200 can embody an elongated U-shaped channel comprising two sidewalls and a bottom wall located therebetween. An open passage is provided with the housing 200 that runs generally parallel to the bottom wall. The distal end of the housing 200 can include an enclosed or continuous perimeter without any gap, and can have a top surface 230, while the remaining part of the housing can embody an open U-shaped channel. In some example, the distal end can have a gap or a break in one of the surfaces for flexing. Optionally, a housing section or housing slat can be assembled to the U-shaped distal end to form a continuous distal end section. The housing 200 can include a pair of mounting holes 202 for fitment with mounting arms or pins 252 of the support piece 250, slide rails 204 on a top side of the sidewalls 225, a first interior guide groove 206, and a second interior guide groove 208. The second interior guide groove 208 can be located above, elevation-wise, the first interior guide groove 206 and closer to an upper edge of the sidewall 225. In an example, two guide grooves 206, 208 are provided on each sidewall 225 of the U-shaped channel. The various components of the housing 200 are further detailed below.

In exemplary embodiments, the guidewire 390 is provided to aid in positioning of the catheter tube 104 into a vein. Due to the relatively longer length of the cannula or needle 108 of the present assembly 100 and the corresponding longer catheter tube 104 required for accessing the deep vein, the guidewire 390 can be provided to help guide placement of the catheter tube into the vein and prevent or resist kinking of the catheter tube, as further discussed below.

Figure 2:
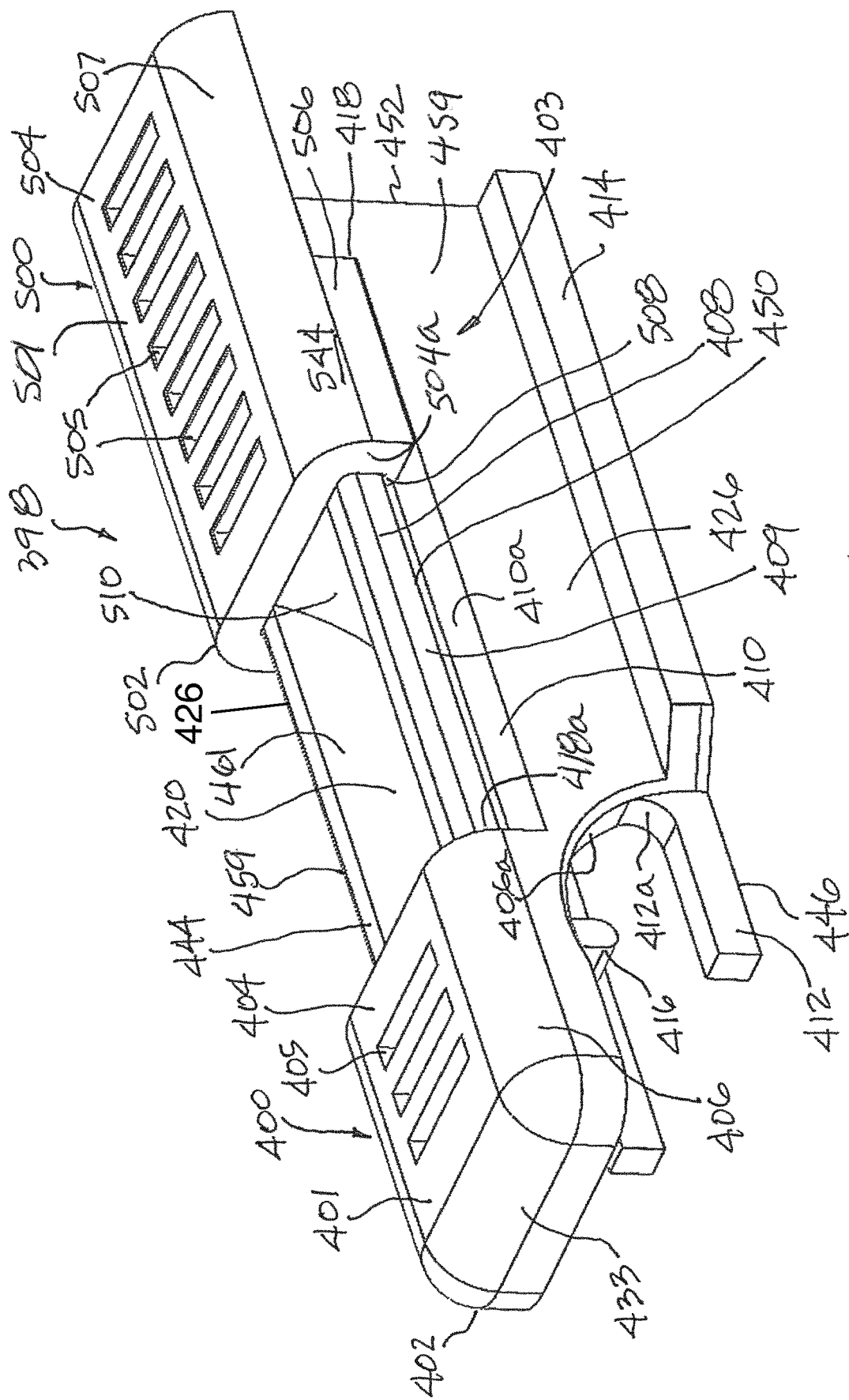
FIG. 2 shows exemplary embodiments of the catheter push tag and the integrated catheter push tag, which can alternatively be called a first catheter push tag and a second catheter push tag.

FIG. 2 illustrates an exemplary embodiment of the catheter push tag 400 and the integrated catheter push tag 500 of FIG. 1, or first catheter push tag and second catheter push tag, respectively. The combination first and second catheter push tags 400, 500 can be referred to as a catheter activation device 398, which has the first push tag 400 and the second push tag 500 and structures for coupling the two, such as the sidewalls 426, as further discussed below. The first and second catheter push tags 400, 500 can move together when the first push tag 400 is activated and can move relative to one another when the second push tag 500 is activated. In an example, the first push tag 400 moves before the second push tag 500 so that the two push tags 400, 500 move together before one moves relative to the other. In an example, the first push tag 400 is connected to the sidewalls 426 of the body section 403 so that movement of the first push tag 400 in the distal direction also moves the two sidewalls 426 in the distal direction. In an example, the first push tag 400 is molded with the two sidewalls 426 as a unitary component.

As the second push 500 is mounted to the sidewalls 426, movement of the sidewalls also moves the second push tag 500 in the distal direction. Subsequently after moving the first push tag 400, as the second push tag 500 is mounted at the respective proximal ends of the two tracks 409 on the two sidewalls 426, the second push tag 500 can slide along the tracks 409 towards a distal position on the tracks, and move relative to the first push tag 400. As further discussed below, this movement of the second push tag 500 in the distal direction can also move the catheter hub 102 in the distal direction to separate from the housing 200.

In an example, the catheter push tag 400 can have a head section 401 and a body section 403 that can be integral, such as being singularly or unitarily formed. The head section 401, which can be arranged at a distal end or portion of the catheter push tag 400, can include a user interface area with a top surface 404 configured for manipulation of the catheter push tag 400 by the user. The head section 401 can include a first side surface 402 and second side surface 406 that are connected by the top surface 404. In an example, the top surface 404 of the head section 401 is generally horizontal and the two side surfaces 402, 406 are generally vertical, or generally orthogonal to the top surface. The head section 401 can additionally include an underside or leg 415 (FIG. 4) extending therefrom, such as extending from the front wall or front side 433 of the head section 401, and the leg 415 having a lip or projection 416. The front side 433 is provided between the first side surface 402 and the second side surface 406. The interface between the front side 433, the first and second side surfaces 402, 406, and the top surface 404 can be chamfered or rounded with smooth transitions.

A body section 403 can extend from a proximal end of the head section 401 in the proximal direction. The body section 403 can be configured to support the integrated catheter push tag 500 and allow the integrated catheter push tag 500 to slide along the length of the body section 403. In exemplary embodiments, the catheter push tag 500 and the body section 403 can have cooperative structure to enable sliding, to enable engagement, or to enable sliding engagement.

The top surface 404 of the head section 401 can have a surface that is generally planar, that is curved or bow-shape, can have a recess, or can generally be shaped to correspond to or cooperate with a digit of the user. An interior cavity or space 420 is provided proximal of the head portion 401. The interior space 420 can be provided between two sidewalls 426 of the body section 403, as further described below. The top surface 404 of the head section 401 can optionally incorporate geometric patterning or indicia 405, which can provide improved grip for the user and/or be for aesthetic purposes. In some embodiments, the geometric patterning 405 can embody recessed strips that are spaced apart or can be formed as cutouts through the wall at the top surface 404 of the head section 401. In some embodiments, the geometric patterning 405 can be spaced apart protrusions or bumps.

The body section 403 can comprise two sidewalls 426 extending proximally from the head section 401. The two sidewalls 426 can include a first side surface 459 and an opposed second side surface 461. In some embodiments, the two side walls 426 extend separately and generally parallel to one another from the head section 401 towards the proximal end, such as in the proximal direction from the head section. The two sidewalls 426 can be spaced from one another as they extend in the proximal direction. In some embodiments, a cross bracing structure can connect the two side walls 426 at a position proximal to the head section 401 to provide structural support, such as a brace, for the two sidewalls. If incorporated, the brace can be anywhere along the length of the two sidewalls 426 of the body section 403, including near the head section 401 or an end opposite the head section or anywhere in between, provided the cross bracing does not interfere with other movable parts or components of the device. Between the two side walls 426 can be the interior cavity or space 420. However, in other embodiments, the head section 401 is formed with the two sidewalls 426 and provide the necessary support without a separate cross-brace or rib.

The two sidewalls 426 of the body section 403 can each have a first side surface 459 and an opposed second side surface 461 as previously described. The first side surface 459, which can be referred to as the exterior surface or exterior-facing surface, can extend in the proximal direction away from the head section 401. The two sidewalls 426 can be a mirror image of one another with minor differences contemplated. Each sidewall 426 can include surface features or contours. In an example, each side wall 426 of the body section 403 can have an upper edge or first edge 444 and a lower edge or second edge 446 and a wall with the wall surface 459 therebetween. Each sidewall 426 can include surface contouring 410, such as rails, channels, and/or guides. In an example, the contouring 410 can include intermediary surfaces 410a sized and shaped for fitment with the integrated catheter push tag 500.

In an example, the intermediary surfaces 410a on each sidewall 426 can embody a recess 450 having a length, or a channel, and the recess 450 can connect to a groove rail 408, which can have a ledge extending away from the central cavity 420 to provide a structure for the integrated push tag 500 to engage. The shape of each groove rail 408 can resemble a track 409 for engagement by the integrated catheter push tag 500 and can be defined by the recess 450, by the intermediary surfaces 410a.

The track 409, which can also be called an upper mating portion, can have a surface inset a predetermined depth from the exterior surface 459 of the sidewall 426. As such, the upper mating portion 409 can have a smaller thickness relative to the remaining portion of the sidewall structure 426 below the intermediary surfaces 410a. In alternative embodiments, the wall thickness can be relatively smaller, equal to or bigger than the remaining portion of the sidewall structure 426, as long size of the track 409 can create a sliding track for the integrated catheter push tag 500. The upper mating portion or track 409 can further have a groove rail 408, wherein the groove rail 408 can be inset from the surface of the upper mating surface. The groove rail 408 can extend along a portion of the length of each side wall 426. As shown, the groove rail 408 terminates short of the proximal most end of the sidewall 426. The proximal end or stop limit 418 of the groove rail 408 can serve as a stop to delimit the proximal travel of the integrated catheter push tag 500 along the two groove rails 408, one on each sidewall 426.

From the position shown in FIG. 2, the integrated or second catheter push tag 500 is limited from further proximal movement by the stop limit 418. However, the proximal position shown, the second catheter push tag 500 is not limited from distal movement. The second catheter push tag 500 can slide or move along the track 409 in the distal direction but can be limited when the front edge 504a of the second catheter push tag 500 abuts the distal stop limit 418a. The distal stop limit 418a can be a proximal surface or shoulder of the head section 401 of the first catheter push tag 400. In other examples, a wall or surface not part of the first catheter push tag 400 can be incorporated to serve as the distal top limit 418a. On the proximal sides of the first and second side surfaces 502, 506, the rear edges of the two side surfaces of the second catheter push tag 500 abut the respective proximal stop limit 418 to limit further proximal movement of the second catheter push tag 500. Optionally, only one proximal stop 418 is utilized.

The two groove rails 408 on the two sidewalls 426 can provide for fitment with the rail protrusions 508 of the integrated catheter push tag 500. For example, the integrated catheter push tag 500 can have a tab or a lip, i.e., rail protrusion 508, that extends from the two side surfaces 506. The tab or lip can be sized and shaped to fit within the recess 450 of the groove rail 408 for sliding engagement. Each rail protrusion 508 can extend the full length of the respective side surface 502, 506 or less than the full length. In some embodiments, each groove rail 408 can be located adjacent to an intermediary surface 410a where the groove rail 408 meets with the upper mating portion or track 409. Alternatively, the two groove rails 408 and the two rail protrusions 508 on the integrated catheter push tag 500 can be switched so that the integrated catheter push tag 500 incorporates two groove rails and the two sidewalls 426 each incorporates a rail protrusion.

Accordingly, when the rail protrusions 508 are coupled with the groove rails 408, the integrated catheter push tag 500 is slidable along the length of the groove rails 408. The engagement of the rail protrusions 508 and the groove rails 408 deter or restrict unwanted separation between the integrated catheter push tag 500 and the body section 403. In this way, when the rail protrusions 508 of the catheter push tag 500 are slidably fitted to the groove rails 408, the exterior sides 544 of the integrated catheter push tag 500 are generally flush with the exterior sides 459 of the wall structures of the two sidewalls 426 of the body section 403 of the catheter push tag 400. In some examples, the exterior sides 544 of the integrated catheter push tag 500 can extend further outwardly, away from the central lengthwise axis of the body section 403, than the wall surfaces 459 of the sidewalls 426.

In some embodiments, the side walls 426 can each include a proximal stop limit 418 and a distal stop limit 418a, which can embody physical structures for stopping movement of the integrated catheter push tag 500 in the proximal direction and the distal direction, respectively. For example, the stop limits 418, 418a can embody wall structures adjacent the groove rail 408 to provide physical barriers for the rail protrusions 508 on the integrated catheter push tag 500. The stop limits 418, 418a can form part of a portion of the body section 403 proximal and distal to the groove rail 408 that do not have the recessing for the intermediary surfaces 410 or the groove rail 408. The stop limits 418, 418a can prevent proximal and distal sliding movements. In this way, it can be visualized that the two groove rails 408 are recessed in an intermediary area of the catheter push tag 400. The stop limits 418, 418a can interface with a first side surface 502 and a second side surface 506 of the integrated catheter push tag 500.

In use, the housing 200 is first advanced to insert the needle tip and the tip of the catheter tube into the vein. Blood flashback is observed before further manipulation of the catheter device 100. In some examples, a visualization tool is used prior to inserting the needle into the vein. Once blood flash back is observed, the housing can be held steady before moving the first push tag. Optionally, the angle of the housing relative to the skin can be lowered before the first push tag is activated. The first catheter push tag 400, such as the head 401, can then advance in the distal direction within the housing 200, which moves the body 403 and the integrated or second catheter push tag 500 mounted to the body 403 in the distal direction. The integrated catheter push tag 500, such as the body 501 of the integrated catheter push tag, can then advance in the distal direction along the rails 408. The first and second catheter push tags 400, 500 therefore can move together as a unit and then the second catheter push tag 500 can move relative to the first catheter push tag 400 in the distal direction while the latter remain stationary.

The first and second catheter push tags 400, 500, such as the head section 401 and the body 501, are spaced from one another a first distance when the first catheter push tag 400 moves in the distal direction. The distance between the first and second catheter push tags 400, 500 is narrowed, and can even be zero, when the second catheter push tag 500 moves relative to the first catheter push tag 400 in the distal direction. The second catheter push tag 500 can touch the first catheter push tag 400 when the second catheter push tag 500 moves relative to the first catheter push tag 400.

The integrated catheter push tag 500 can have a generally U shape structure or body 501 when viewed from an end view or from an end cross-section and can comprise a first side surface 502, a top surface 504, and a second side surface 506 (FIG. 2). The top surface 504 can couple to the first side surface 502 and the second side surface 506 through chamfered or radiused surface portions 507. The first side surface 502 and the second side surface 506 of the integrated catheter push tag 500 can extend at least a portion of the length of the top surface 504 of the integrated catheter push tag 500 and the radiused portion 507 can extend the full length of the top surface 504, or can extend short of the full length.

At a bottom side of the first side surface 502 and the second side surface 506 can be the rail protrusions 508 extending inwardly to engage the groove rail 408 of the body section 403. The rail protrusions 508 can extend along the length of the first side surface 502 and the second side surface 506. In some embodiments, the rail protrusions 508 extend only along a portion of the length of the first side surface 502 and the second side surface 506. As previously discussed, the rail protrusions 508 extend inwardly from the first and second side surfaces 502, 506 to engage the respective groove rails 408 on the two sidewalls 426. The proximal end of the integrated catheter push tag 500 can extend further proximally than the end edge 452 of the two sidewalls 426 in the proximal position of the integrated catheter push tag 500. In some examples, the proximal end of the integrated catheter push tag 500 can extend even with the end edge 452 of the two sidewalls 426 in the proximal position of the integrated catheter push tag 500, or less preferably can be located distal of the end edge 452 of the two sidewalls 426.

The top surface 504 of the integrated catheter push tag 500 can be shaped to cooperate with a digit of the user. The top surface 504 can have geometric patterning 505, which can provide improved grip for the user or be for aesthetic purposes. In some embodiments, the geometric patterning 505 can be recessed cutouts. In some embodiments, the geometric patterning 505 can be protrusions or bumps. Curved or recessed surfaces can optionally be incorporated to improve gripping between the top surface and a user's finger.

The first catheter push tag 400 can include distal guides 412 projecting from the body section 403. In an example, one distal guide 412 projects distally from a distal portion of each sidewall 426. The two distal guides 412 can aid in lateral stabilization and guidance of the catheter push tag 400 in the housing 200 when the user manipulates the head section 401. Each distal guide 412 can have a generally square or rectangular cross-section and a length extending distally of the distal end of the sidewall 426, such as the curved section 406a of the sidewall. The two distal guides 412 can be inset from the exterior surfaces of the side walls 426 to allow for a clearance for ready sliding and can extend distally short of the front side or front wall 433. Each distal guide 412 can have an arcuate or curved proximal end 412a to from a smooth contour with the curved section 406a of the side wall 426.

Additionally, the body section 403 of the catheter push tag 400 can further include exterior guide protrusions 414. In an example, one exterior guide protrusion 414 projects radially outwardly from each of the sidewalls 426 away from the cavity or space 420 of the body section 403. Each exterior guide protrusion 414 can protrude outwardly from the exterior surface 459 of the sidewall 406 and can extend substantially along the length of the sidewall 426, near or adjacent the lower edge 446. In an example, each exterior guide protrusion 414 can extend radially relative to the lengthwise axis of the body section 403 from a first end of the sidewall 426 to a second end of the sidewall. In other examples, the exterior guide protrusion 414 extends from a position proximal of the distal guide 412 to a position substantially co-planar with the end edge 452 of the sidewall 426. In other examples, the exterior guide protrusion 414 can embody two or more sections that can extend up to or short of the end edge 452. Each exterior guide protrusion 414 can extend orthogonally from a sidewall 426. The exterior guide protrusions 414 can be sized and shaped to correspond to the two first interior guide grooves 206 of the housing 200 (FIG. 1). In an example, the exterior guide protrusions 414 are configured for sliding engagement with the two lower first interior guide grooves 206 of the housing 200, as further discussed below.

Figure 3:
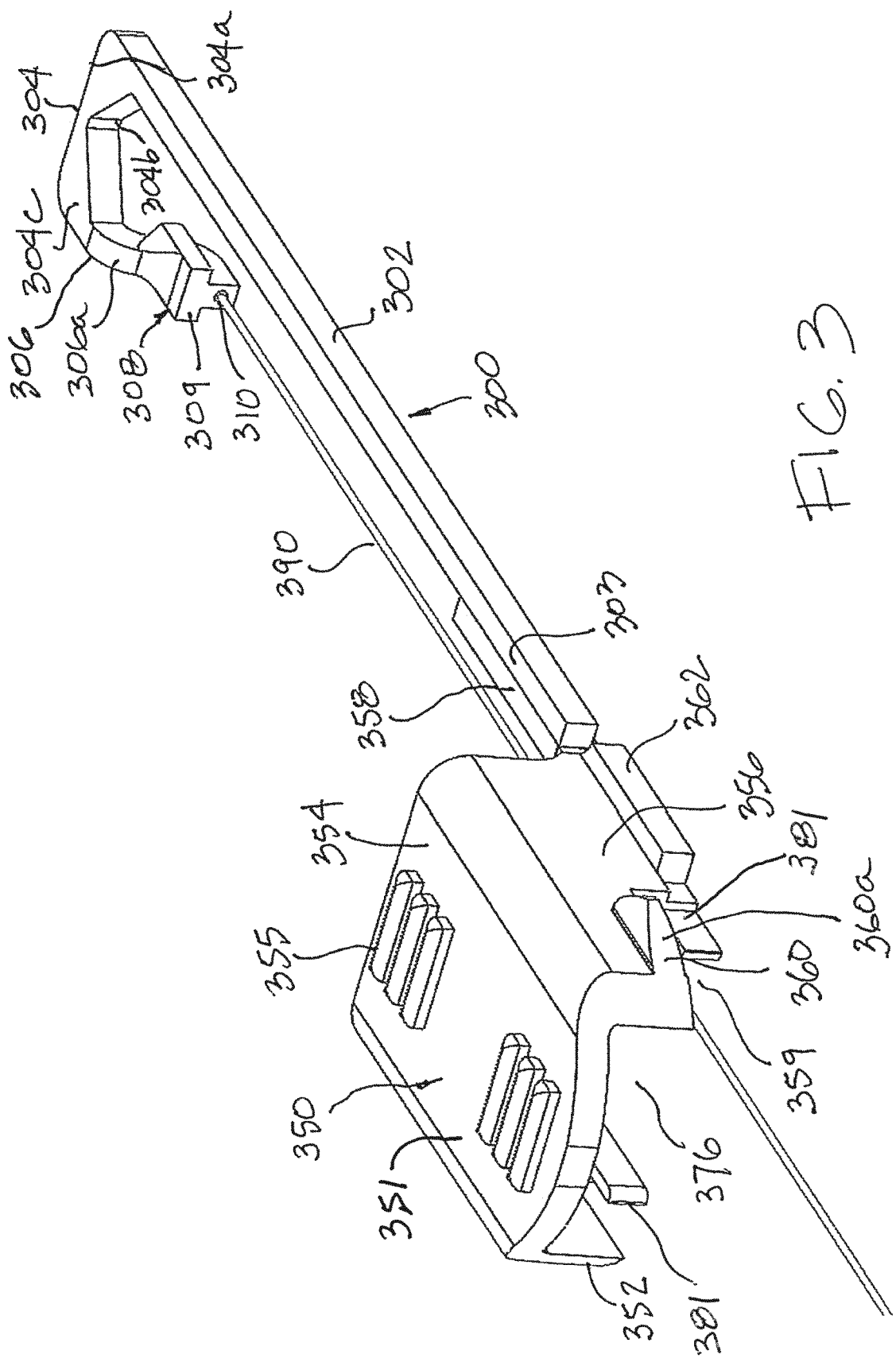
FIG. 3 shows exemplary embodiments of the guidewire push tag and the C bracket.

FIG. 3 illustrates an exemplary embodiment of the guidewire push tag 350 and the bracket 300 shown in FIG. 1. The guidewire push tag 350 can have a generally U shape structure or body 351 from an end view comprising a first side surface 352, a top surface 354, and a second side surface 356. The top surface 354 can be shaped to correspond to or cooperate with a digit of the user. The top surface 354 can have geometric patterning 355, which can provide improved grip for the user or be for aesthetic purposes. In some embodiments, the geometric patterning 355 can embody recessed cutouts. In some embodiments, the geometric patterning 355 can be protrusions or bumps. The side surfaces 352, 356 can have surface features and non-uniform edges.

The first side surface 352 and the second side surface 356 of the body 351 of the guidewire push tag 350 can be coupled to the top surface 354 at upper edges. In an example, the first and second side surfaces 352, 356 are unitarily formed with the top surface 354, such as by injection molding. A bracket or frame 300 can be provided with the body 351, such as be positioned proximally of the body 351 of the guidewire push tag 350. In an example, the bracket 300 can have a first arm 302 located to one of the side surfaces of the guidewire push tag 350. As shown, the bracket 300 is coupled to the elongated extension 358 and extends from the second side surface 356 with extension from the first side surface 352 being optional. The elongated extension 358 can be unitarily formed with one of the side surfaces 352, 356 of the body 351.

In an example, an elongated extension 358 extends from a proximal edge of the second side surface 356 of the guidewire push tag 350. The elongated extension 358 can have a generally square cross-section and can have a length that is about 50% to 150% of the length of the second side surface 356. However, the length of the elongated extension 358 is not limited to the disclosed range and can vary, such as being longer than 150% of the length of the second side surface 356. The polygonal shaped cross-section of the elongated extension 358 can include a first side edge. The bracket 300 can be secured to the first side edge of the elongated extension 358, as shown in FIG. 3. In an example, the bracket 300 is bonded or glued to the elongated extension 358, such as to the first side edge of the elongated extension 358. In an alternative embodiment, the bracket 300 can be connected differently, such as by welding or by tight fitting to the elongated extension 358, or be connected to the inner side of the elongated extension 358.

In an example, the first and second side surfaces 352, 356 of the body 351 of the guidewire push tag 350 each comprises a distal end or portion 359 that is irregular, undulating, and/or includes contoured portions. In an example, the distal portion 359 is other than a square or straight edge corner. As shown in FIG. 3 and further discussed below, the distal portion 359 at each side surface can include a cut out so that portions of the guidewire push tag 350 can be located within the interior of the housing 200 while other portions of the guidewire push tag 350 can locate above the housing 200 and rest on the two slide rails 204 of the housing, as further discussed below.

Along each of the two bottom edges of the first side surface 352 and the second side surface 356, there can be an exterior guide protrusion 362 protruding outwardly away from a central portion or cavity 376 of the guidewire push tag 350. The two exterior guide protrusions 362 can ride against the underside of the two slide rails 204, opposite the rest wings 360. In an example, the guidewire push tag 350 can have a rest wing 360 projecting generally perpendicular from the first side surface 352 and from the second side surface 356. As shown, the two rest wings 360 are located generally closer to a distal end or distal portion of the guidewire push tag 350 than the proximal end or portion of the body 351. Each rest wing 360 can have a curved or contoured edge 360*a* to match the shaped distal portion of the housing 200 (FIG. 7).

The exterior guide protrusions 362 can extend along a portion or the entire length of each of the first side surface 352 and the second side surface 356 of the body 351 of the guidewire push tag 350, or optionally can extend less than the full length. The exterior guide protrusions 362 can be located at a bottom edge of the first side surface 352 and the second side surface 356 when assembled. The exterior guide protrusions 362 can be sized and shaped to correspond to the second interior guide groove 208 of the housing 200 (FIG. 1).

Two actuation bars 381 can be provided with the guidewire push tag 350. As shown in FIG. 3, the two actuation bars 381 can be located adjacent the two side surfaces 352, 356. In a particular example, the two actuation bars 381 can be formed with the guidewire push tag 350, such as being unitarily formed in a plastic injection molding process. With reference to FIG. 5, which shows the extended dwell catheter assembly 100 without the U-shaped body 351 of the guidewire push tag 350 for discussion purposes, the two actuation bars 381 can be provided to interact with the two rotation stops 254 on the support piece 250. For example, the two actuation bars 381 can compress or move the two rotation stops 254 closer together to release the support piece 250 from the restriction imposed by the limiting walls 213 formed with the housing 200. If the two rotation stops 254 are not squeezed or moved closer together, then the side warms 256 would interfere with the two limiting walls 213. However, by squeezing the two rotation stops 254 together, this then allows the support piece 250 to rotate about the axis defined by the mounting arms 252 to rotate the central body 258 away from the path of the catheter hub 102 to enable separation of the catheter hub 102 from the housing 200. The actuation bars 381 and/or the rotation stops 254 on the support piece 250 can have tapered surfaces to allow engagement so that the actuation bars can compress the two rotation stops 254 therebetween to free the support piece 250 from the constraint of the housing, as further discussed below. In other examples, the support piece 250 can be restricted from rotation and the mechanism formed with the guidewire push tag 350 for freeing the support piece 250 to rotate can be other than as described. For example, a peelable adhesive or a detent can be used and the guidewire push tag 350 can sever or separate the adhesive or the detent.

Extending in a rearward, in a proximal direction from the body 351 of the guidewire push tag 350, can be a mounting portion or elongated extension 358 (FIG. 3). The mounting portion 358 can extend from a bottom edge of one of the first side surface 352 and the second side surface 356. In an exemplary embodiment, the mounting portion 358 can extend from a bottom edge of the second side surface 356. The mounting portion 358 can be rectangular in shape and have a rectangular or polygonal cross section as it extends in the proximal direction from the guidewire push tag 350.

The bracket 300 can have a first arm 302 with a mounting portion 303 at a first end and a hook section or portion 304 at an opposed, second end. The first arm 302 and the hook section or portion 304 can define a J-shape structure when viewed from above. The first arm 302 can be generally uniform as it extends from the distal end to the proximal end just before transitioning to the hook section 304. In some examples, the first arm 302 can have a square cross-sectional shape or T-shape cross section. The mounting portion 303 can unitarily formed with the first arm. The mounting portion 303 can simply be a distal end part of the first arm 302. The mounting portion 303 can be secured to the mounting portion 358 of the guidewire push tag 350. In some examples, the mounting portion 358 of the guidewire push tag 350 and the mounting portion 303 of the bracket 300 can include a tongue and a groove combination, detents, pin and hole, or other mechanical means to facilitate coupling the two together. In other examples, the two can be bonded or welded together. Optionally, the two mounting portions can be co-molded or insert molded together.

The hook section 304 can extend from the first arm 302 and can be unitarily formed therewith. The hook section 304 and the first arm 302 can both have upper or tip surfaces that are co-planar or one can be recessed from the other and can be parallel to one another. The hook section 304 can alternatively be coupled to the first arm 302, such as by detents with optional adhesive. The hook section 304 can have a proximal end or edge 304a and a distal end or edge 304b. The proximal edge 304a can be smooth or have a flat end surface while the distal end 304b can have a tapered shape that narrows in cross section at a central portion with an apex and widens at portions coupling to the first arm 302 and the second arm 306. The second arm 306 can be located on the opposite end of the hook section 304 from the first arm 302.

In some examples, the elongated extension 358 and the bracket 300 can be eliminated and the guidewire 390 can be attached directly to the body 351 of the guidewire push tag 350. For example, where the elongated extension 358 and the first arm 302 are provided, a metal wire length can connect to the body of the guidewire push tag 350. The metal wire length can be sized with a gauge that does not readily flex or bend. Where the hook section 304 is currently provided, a U-shape bent can be provided with the metal wire length. A contoured section can be provided with the U-shape bent to align to a guidewire length, which can be welded or coupled to the metal wire length using a mechanical coupling. A guidewire 390 can thus be provided with the bracket but by using a sufficiently heavy metal wire extending from the guidewire push tag 350.

The second arm 306 can have an angled portion 306a that angles downwardly, elevation-wise, to offset a guidewire holder 308 from a plane 304c formed by the first arm 302 and the hook section 304. In some embodiments, the angled portion 306a of the second arm 306 can be a smoothly curved portion to offset the guidewire holder 308. Alternatively, the second arm 306 can have a sharp angular portion to generate the planar offset. In yet other examples, the guidewire holder 308 can extend from a vertical drop or a bar that extends from the second arm 306. In still other examples, the first arm 302 can have an offset near the mounting portion 303 so that the first arm and the hook portion 304 can extend generally along the same plane. In other words, the offset can be provided away from the hook portion.

The offset provided by the angled portion 306a can change the position of the guidewire holder, elevation-wise, so that the guidewire 390 attached thereto can align with the catheter tube of the needle assembly following assembly of guidewire push tag 350 and the bracket 300. The guidewire holder 308 can have a rectangular base 309 coupled to the second arm 306, wherein the rectangular base 309 flares out, such as having a wider body, from the second arm 306 to create an enlarged cross-sectional shape. The rectangular base 309 has a guidewire hub 310 extending therefrom, which can be unitarily formed with the rectangular base 309. A recess or hole can be provided with the guidewire hub 310 to hold the guidewire 390, optionally with adhesive. In an assembled state, the guidewire 390 can extend in a parallel direction to the first arm 302.

Accordingly, when the guidewire push tag 350 and the bracket 300 are assembled as an integral unit, they take on a C shape with the push tag 350 and the hook section 304 serving as end pieces of the C, when viewed from above. In an assembled state, the guidewire 390 extends in distally from the guidewire hub 310 and extends between the first side surface 352 and the second side surface 356 of the guidewire push tag 350. In exemplary embodiments, the guidewire push tag 350 and the bracket 300 are sized and shaped so that the guidewire 390 passes down a middle section between the two side surfaces 352, 356.

During use, distal movement of the body 351 of the guidewire push tag 350 moves the bracket 300 attached to the body 351 distally forward, which also moves the hook portion 304 and the guidewire hub 310 in the distal direction. As the guidewire 390 is attached to the guidewire hub 310, the guidewire 390 is moved distally by distal movement of the guidewire push tag 350. Further, distal movement of the guidewire push tag 350 moves the two actuation bars 381 in the distal direction. With further reference to FIG. 5, shown without the body 351 of the guidewire push tag 350, the two actuation bars 381 are configured to move distally by the guidewire push tag 350 to interact with the rotation stops 254 to move the two side arms 256 of the support piece inwardly closer together to allow the support piece 250 to free itself from the constraint of the limiting walls 213, as previously discussed.

Figure 4:
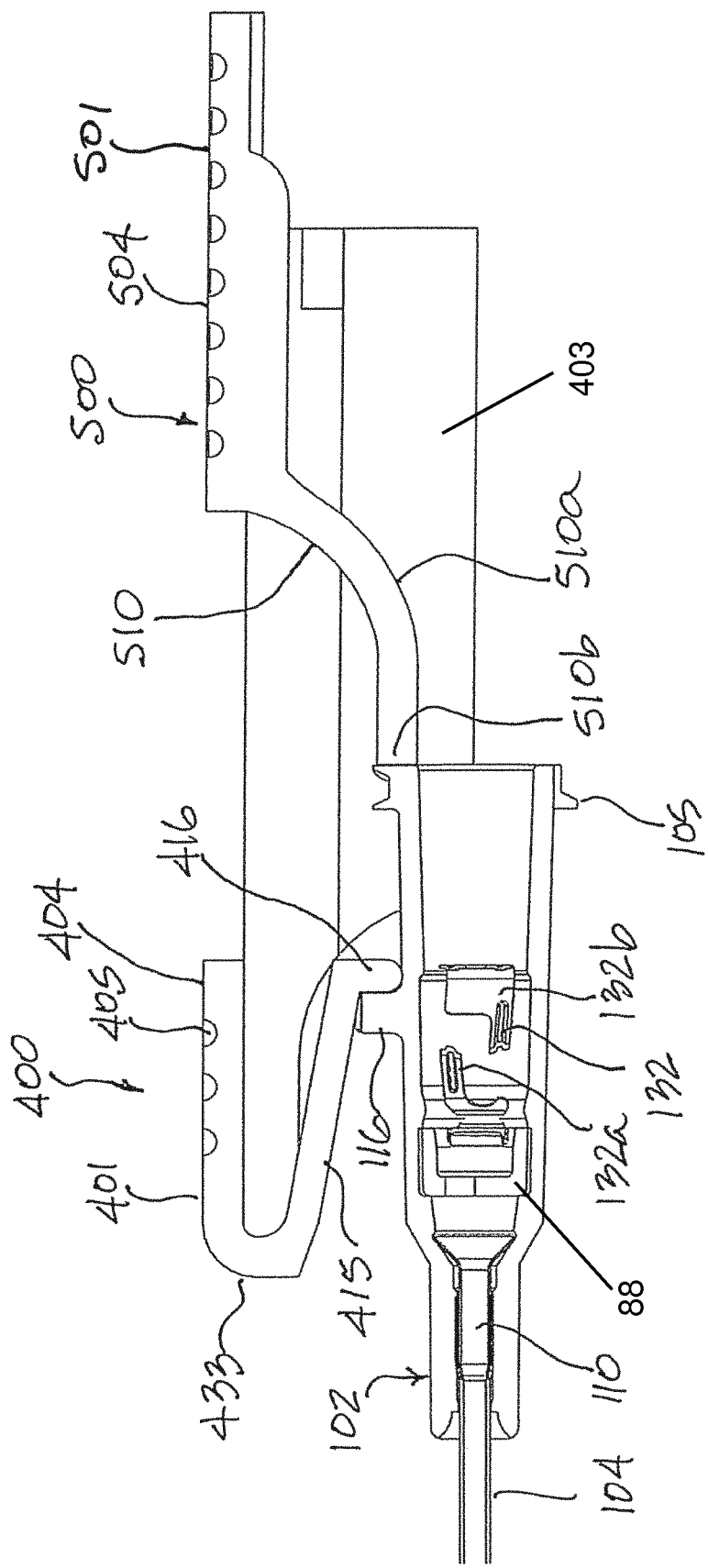
FIG. 4 shows a cross-sectional view of exemplary embodiments of the catheter hub, the catheter push tag, and the integrated catheter push tag in an assembled, un-activated state.

FIG. 4 illustrates a cross-sectional view of an exemplary embodiment of the catheter hub 102 with exterior threads 105 at a proximal end, the catheter push tag 400 and part of the body section 403, and the integrated catheter push tag 500 in an assembled, un-activated state with the catheter push tag 500 in the proximal position. The catheter hub 102 can be generally understood as having a conical or cylindrical shape with a female Luer taper at the proximal open end, as would be understood by one of ordinary skill in the art.

The catheter tube 104 extends from the catheter hub 102, as shown in the cross-sectional view, and retained to the catheter hub by a bushing 110. The bushing 110 can be configured to wedge the proximal end of the catheter tube 104 against the interior wall surfaces of the catheter hub 102 to retain the catheter tube 104 to the catheter hub 102.

The catheter hub 102 can include a safety shield or needle guard 132 disposed in an interior of the catheter hub 102. The safety shield 132 can be provided to guard the tip of the cannula or needle 108 when the cannula is separated from the catheter hub 102 following successful placement of the catheter tube into the patient. On withdrawal of the hollow needle 108 from the catheter hub 102 following successful venipuncture, a change in profile 144 provided near the needle tip and having the form of a radial projection on the hollow needle, such as by crimping, engages the safety shield 132, such as the opening on the proximal wall of the safety shield, so that the safety shield 132 can be removed from the catheter hub with the needle 108.

Exemplary information regarding safety shields can be found in U.S. Pat. Nos. 7,736,339 and 8,382,721, the contents of which are expressly incorporated herein by reference. An exemplary safety shield 132 can have two arms 132a, 132b arranged on either side of a median plane defined by the needle shaft in an un-activated state. When the needle is retracted through the catheter tube 104 during separation, the needle tip 108a can move proximal of the two distal walls of the two arms, allowing the two arms to move, such as to spring or deflect radially to cover the needle tip to prevent unintended needle sticks. In other examples, the change in profile 144 can include a sleeve, a notch, or a material buildup on the shaft of the needle. In yet other examples, the needle guard 132 can have a single arm or two arms that extend along the length of the shaft without crossing the needle axis.

In embodiments, when the needle 108 is removed from the catheter hub 102, the safety shield 132 can be held generally stationary inside the catheter hub 102 until the change in profile 144, such as a crimp, near the needle tip comes to abut on a rear proximal wall of the needle guard and the needle tip moves proximally of the two distal walls on the safety shield 132. At this point, the two spring arms, which are no longer biased outwardly in the radial direction by the needle, spring inwards to cover the needle tip 108a, whereupon the safety shield 132 with the needle 108 can be removed from the catheter hub 102.

The needle guard or safety shield 132 can be made of thin metal sheet being stamped into the desired shape and then cold worked or formed, such as bent, into final shape wherein, in the biased position, one or two elbows of the safety shield engage or engages the catheter hub and in the unbiased position the safety shield disengages from the catheter hub and move radially to a smaller radially profile so that the needle guard can pass through a small internal diameter section of the catheter hub.

The catheter hub 102 can include a retaining tab or push tab 116 projecting perpendicularly or radially outwardly from the outside surface of the catheter hub 102. The retaining tab 116 can be generally rectangular in shape with other shapes contemplated and can be used as a leverage point of structure. For example, the leg 415 on the first catheter push tag 400 can push against the push tab 116 to advance the catheter hub 102 in the distal direction. In an example, a lip or retaining portion on the leg 415 can push on the push tab 116.

As noted with respect to FIG. 2, the exemplary catheter push tag 400 can include an underside or leg 415 having a retaining portion 416 (FIG. 4) extending from the head section 401, which has the top surface 404 with geometric patterning 405. The bent back leg 415 from the front side 433 can act like a leaf spring and form part of a leverage with the retaining portion 416. The retaining portion 416 can be at an end of the bent back leg or leg 415. The bent back leg 415 can be angled as shown in FIG. 4 and can deflect by moving upwardly towards the top surface 404 of the head portion 401 of the catheter push tag 400 during installation. The leg 415 can be made of a material that allows for elastic deformation. In the un-activated assembled state, the bent back leg or leg 415 can position the retaining portion 416 such that it can act on the retaining tab or push tab 116 of the catheter hub 102 to retain the catheter hub 102 and prevent the catheter hub from accidental separation from the assembly 100.

The retaining portion 416 can exert force in a direction along the axis of the catheter hub 102. For example, when moving the catheter push tag 400 in the distal direction during use, the retaining portion 416 can push the push tab 116 in the distal direction to then advance the catheter hub 102 and the catheter tube 104 in the distal direction. Advancing the catheter push tag 400 also moves the body section 403. As the integrated catheter push tag 500 is mounted to the body section 403 and the integrated catheter push tag 500 has a pushing leg 510, movement of the first catheter push tag 400 in the distal direction also moves the integrated catheter push tag 500, which causes the push end 510b of the pushing leg 510 to push the catheter hub 102 in the distal direction. As further discussed below, the catheter push tag 400 can be pushed distally after initial catheterization with the needle and following advancement of the guidewire push tag 350 to advance the guidewire 390 into the vein to facilitate guiding the catheter tube 104. Then the integrated catheter push tag 500 can advance to move the catheter hub 102 in the distal direction.

Figure 4A:
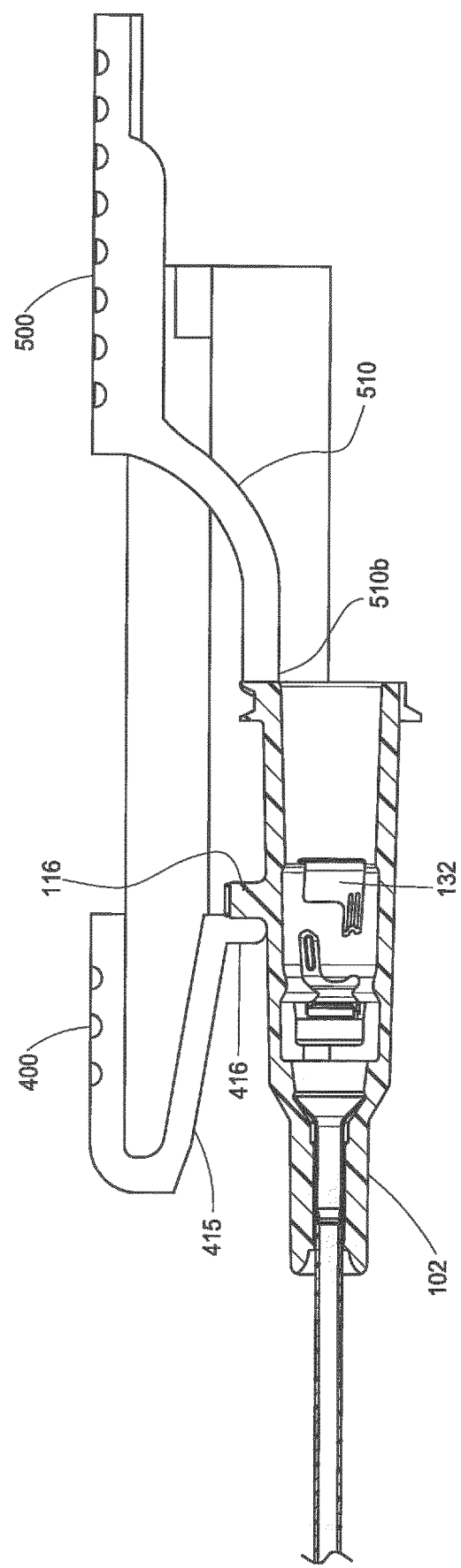
FIG. 4A shows a cross-sectional view of an arrangement in which the retaining portion of the underside leg 415 is located distally of the push tab.

With reference to FIG. 4A, an alternative arrangement shows the retaining portion 416 located distally of the push tab 116. Thus, movement of the catheter push tag 400 in the distal direction also moves the catheter hub 102 in the distal direction via the push end 510b of the push leg 510 pushing on the catheter hub 102 as described above. An advantage of locating the retaining portion 416 distally of the push tab 116 as shown in FIG. 4A is that it provides a user with the option to move the catheter push tag 400 in the proximal direction to cause the retaining portion 416 to push the push tab 116 in the proximal direction to move the catheter hub 102 in the proximal direction.

The integrated catheter push tag 500 can be slidably mounted to the catheter push tag 400 which has a body section 403, as previously described with reference to FIG. 2. Thus, the integrated catheter push tag 500 can slide with the body section 403, such as when located at a proximal position of the body 403 and the catheter push tag 400 is advanced in the distal direction, and can slide relative to the body section 403 by placing a finger on the body 501 of the integrated catheter push tag 500 and advancing the body 501 relative to the head section 401 of the first catheter push tag 400, as further discussed below.

The integrated catheter push tag 500 can have a top surface 504. The integrated catheter push tag 500 can include a push leg 510. The push leg 510 (FIGS. 1 and 4) can extend from a distal end of the top surface 504. The push leg 510 can have a curved portion 510a and a pushing portion or push end 510b. The curved portion 510a can be sized and shaped to extend downwardly, elevation-wise, from the body of the integrated push tag 500 and can have a width that fits within the width of the cavity 420 between the two sidewalls 426 of the body section 403. The pushing portion or push end 510b of the leg can be aligned to contact or abut a proximal end of the catheter hub 102. The pushing portion 510b can exert a force on the catheter hub in a distal direction along the axis of the catheter hub 102 to advance the catheter hub in the distal direction. For example, when the integrated catheter push tag 500 is advanced in the distal direction after the first catheter push tag 400 advances the catheter hub in the distal direction, the pushing portion or push end 510*b* is also advanced to then push the catheter hub 102 in the distal direction. When pushed by the integrated catheter push tag 500, the push tab 116 moves distally and separates from the retaining portion 416 of the bent back leg 415. Additional implementation of the elements can be seen in FIGS. 8-12.

FIG. 5 illustrates a cross-sectional perspective view of an exemplary embodiment of the housing 200 taken along a horizontal plane cutting through the mounting holes 202 for receiving the pins of the support piece 250. One mounting hole 202 is provided on each sidewall of the housing 200. FIG. 5 illustrates the positioning of the support piece 250 in an assembled state. The support piece 250 is optional but preferred for steadying or supporting the needle and the catheter tube to prevent or limit kinking of the needle 108 and catheter tube 104 during at least part of the advancement of the guidewire 390. In the assembled state, the support piece 250 has the mounting pins 252 inserted in the mounting holes 202. The support piece 250 can have a generally W shape body, the W shape body defined by two side arms 256 and a central body piece 258. In an example, the two side arms 256 are each generally rectilinear in configuration and each having at least two spaced apart side edges.

The two side arms 256 are each spaced from the central body piece 258 by a gap and connect to the central body piece 258 along lower joining sections, near a cutout 260. The central body piece 258 can have a blunt tapered tip, which define enlarged gaps between the central body piece 258 and the two side arms 256 at the tapered tip end of the central body piece. These enlarged gaps provide added clearance for the two side arms 256 to compress or move into during assembly of the mounting pins 252 into the mounting holes 202 and during deflection of the two side arms 256 when activating the support piece 250 by the actuation bars 381 on the guidewire push tag 350 to allow rotation of the support piece 250 away from the path of the catheter hub 102 to permit distal movement of the catheter hub 102 out the distal end of the housing 200, as further discussed below.

The mounting pins 252 can attach to the two side arms 256 and then project outwardly to define a rotational axis. The pins can be generally round. The mounting pins 252 can further include rotation stops 254 projecting radially outward from the mounting pins 252, one on each mounting pin. Each rotation stop 254 can extend perpendicularly from the axis defined by the corresponding mounting pins 252. As shown, the rotation stop 254 can include a ramp surface so that the two ramp surfaces of the two rotation stops 254 can be pressed together by the actuation bars 381 located on the guidewire push tag 350 (FIGS. 3 and 5). In an example, the support piece 250 is made from a plastic material with options to produce the support piece from other materials, including from metal. The support piece 250 can be unitarily formed as a single unit or can be assembled from multiple components.

The central body piece 258 of the support piece 250 can include a radiused cutout 260 corresponding to the catheter tube 104. In an example, the cut out 260 has a width that is about the same size as the diameter of the catheter tube or can be slightly larger, such as by 0.5 thousandths to about 5 thousandths larger. However, the dimensions are not limited and can have other working ranges. As shown, the curved central portion 260*a* of the cutout 260 is configured to contact the catheter tube 104 to help guide the catheter tube and the needle located therein between the housing lower surface 200*a* and the cutout 260*a* during cannulation. In some examples, the housing lower surface 200*a* can include pre-formed shape to facilitate guiding the catheter tube. For example, a channel having an arc shape can be provided on the housing lower surface 200*a* to help guide the catheter tube and the needle located therein.

The radiused cutout 260 can contact and support the catheter tube 104 and the needle located therein to lessen deflection of the catheter tube 104 and the needle inside the catheter tube 104 during insertion into a patient and during advancement of the guidewire 390. Thus, the catheter tube 104 and the needle 108 inside the catheter tube can be supported between the support piece 250 and the housing bottom surface to limit or prevent the catheter tube and the needle from kinking and/or flexing during advancement of the needle and catheter tube following initial catheterization and verification of proper vein placement and advancement of the guidewire. The angle between central body piece 258 and the rotation stops 254 can be obtuse. The support piece 250 releases upon advancement of the guide wire.

In an example, the two side arms 256 can define a width and the width of the two side arms can be larger than the width or gap defined by the two limiting walls 213 on the nose section 215 of the housing 200. The differences in dimensions forces the support piece 250 to remain angled as shown in FIG. 5, due to the two limiting walls 213 restricting movement of the two side arms 256, to provide support between the support piece 250, and in particular the cutout 260, and the housing lower surface 200*a* to support the needle. As further discussed below and alluded to above, the support piece 250 can be activated to rotate about the axis defined by the two mounting pins 252 to then allow the catheter hub to advance distally of the support piece. For example, the two side arms 256 can be forced to squeeze through the gap defined by the two limiting walls 213, such as by deflecting two arms together, to then allow rotation. In an example, the guidewire push tag 350 is provided with a pair of actuation bars 381. When the guidewire push tag 350 is advanced in the distal direction to advance the guidewire, the pair of actuation bars 381 formed with the guidewire push tag 350 squeeze the two rotation stops 254 inwardly together and inwardly relative to the lengthwise axis of the housing 200. This then forces the two side arms 256 together to free the support piece from the constraint of the two limiting walls 213 to then allow the support piece to rotate about the mounting arms 252. Distal advancement of the catheter hub provides the rotational force for rotating the support piece.

FIG. 6 illustrates a partial perspective view of the housing 200. To illustrate additional details, exemplary embodiments of the housing 200 can have a retention block 210. The retention block 210 can be located at an intermediary position along an interior of the housing 200. In an example, the retention block 210 is formed with the housing. In another example, the retention block 210 is separately formed and attached or secured to the housing 200. The retention block 210 can be a raised feature in the interior of the housing 200, protruding from a bottom interior surface 216 of the housing 200. In some embodiments, the retention block 210 can be generally rectangular, protruding from the bottom interior surface 216. The retention block 210 can include a central through opening 212 extending along the proximal to distal direction of the housing 200. In embodiments, the needle 108 can be fixed to the retention block 210 by mechanical means, by adhesive, or both. Thus, the retention block 210 can function or operate as a needle hub as it retains or holds the needle 108. As described below with reference to FIGS. 8-12, the retention block 210 can provide for retention of the needle 108 and as a movement limiter for the guidewire 390. In embodiments, the guidewire holder 308 is located on a proximal side of the retention block 210 when the needle assembly is assembled. The guidewire 390 can pass through the opening 212 of the retention block 210 and through the lumen of the needle 108 towards a distal end of the assembly 100. Accordingly, when the bracket 300 is moved by manipulation of the guidewire push tag 350, the bracket 300 can be limited in its maximum travel when the guidewire holder 308 contacts the proximal side of the retention block 210.

The retention block 210 can also include a top surface 214, which can be sized and shaped to allow movement of the push leg 510 on the integrated catheter push tag 500 past the retention block 210 or act as a guide against deflection of the push leg 510.

FIG. 7 illustrates a perspective view of an exemplary embodiment of an extended dwell catheter assembly 100 in an assembled state, with the guidewire push tag 350 shown advanced distally to its distal position to illustrate the catheter push tag 400. In the assembled state, the components of FIGS. 2-5 are coupled with the housing 200. Accordingly, in the assembled state, the guidewire push tag 350, the catheter push tag 400, and the integrated catheter push tag 500 are all slidably coupled to the housing 200. Additionally, the back cover 600 can cover at least one of the push tags to prevent accidental, false activation, of the one or more covered push tags. In some examples, the cover 600 can be omitted or can be singularly formed with the housing 200. The push tags can be said to be stacked in that, in the assembled state, the cover 600 is attached to the housing 200 and is stacked above and covers the integrated catheter push tag 500 and only the guidewire push tag 350 is exposed, as shown in FIG. 8. Further, the guidewire push tag 350 is stacked over or above the catheter push tag 400 in the ready to use position of the device 100. Thus, the catheter push tag 400 is shown in FIG. 7 only following advancement of the guidewire push tag 350 to the distal position to expose the catheter push tag 400, which is otherwise normally covered by the guidewire push tag in the ready to use position. When the catheter push tag 400 is then moved in the distal direction after movement of the guidewire push tag 350, movement of the catheter push tag 400 can move the body section 403 (FIG. 2) and the integrated catheter push tag 500 in the distal direction due to the stacking of the integrated catheter push tag 500 to the body section 403 of the catheter push tag 400 (FIG. 2).

Additionally, FIG. 7 shows that the rest wings 360 slidably rested on the slide rails 204 of the housing 200. The radiused cutout of the support piece 250 can contact and support the needle through the catheter tube 104 during initial cannulation into a patient. The guidewire push tag 350 is shown advanced to the distal position in FIG. 7, which is the position after the guidewire 390 is advanced following initial cannulation of the needle. Again, the device of the present embodiment is used by first performing cannulation of the needle, such as by holding and advancing the housing 200 to advance the needle tip to puncture the skin, following by advancing the guidewire and then advancing the catheter tube over the guidewire. In the pre-activated position, the guidewire push tag 350 is located proximally adjacent to the distal edge of the back cover 600 and/or overlies the catheter push tag 400.

FIGS. 8-12 illustrate various states or stages of the extended dwell catheter assembly 100 from an initial un-activated state through to separation of the catheter hub after catheterization.

FIG. 8 illustrates a first, un-activated state of the catheter assembly 100. FIG. 8 illustrates the stacking of the various push tags 350, 400, 500 in the un-activated state to prevent accidental, false activation. By having sequential stacking and uncovering of the next push tag through manipulation of the immediate prior push tag, the user can be prevented from accidently manipulating the push tags out of sequence. As shown, the guidewire push tag 350 overlies the catheter push tag 400 or is superjacent the catheter push tag 400 in the first position, or ready to use position of the assembly, and the back cover 600 covers the integrated catheter push tag 500 in a stacking arrangement. As stacked or arranged in the FIG. 8 configuration, only the guidewire push tag 350 is exposed and accessible to be moved by a user. The catheter push tag 400, such as the top surface of the head section of the catheter push tag 400, can be accessed and moved after the guidewire push tag 350 is distally moved to expose the catheter push tag 400. Then after the catheter push tag 400 moves distally to move the body portion 403 distally and the integrated catheter push tag 500 distally, the integrated catheter push tag 500 is now moved distally from the coverage of the back cover 600. The integrated catheter push tag 500 is now exposed and accessible for pushing or manipulating by a user. Thus, the integrated catheter push tag 500 can only move after the catheter push tag 400 is distally moved, as further discussed below.

In the first, un-activated state of FIG. 8, all of the push tags 350, 400, 500 are positioned in their rearmost or respective proximal positions. The guidewire push tag 350 is positioned adjacent and distally of the back cover 600 but not covered, or at least not fully covered by the back cover. In this position, the bracket 300 (FIG. 3) is in a rearward position near the proximal end of the assembly 100. As shown, the guidewire 390 passes through the opening 212 of the retention block 210 and through the needle 108. In the ready position, the proximal edge body of the guidewire push tag 350 contacts the distal edge of the cover 600 with a gap between the two contemplated. In an example, the top surface of the guidewire push tag 350 is generally flushed with the top surface of the back cover 600. A light gap can be provided near the inside surface of the guidewire push tag 350 and the top surface of the head section of the catheter push tag 400 to avoid interference so that movement of the guidewire push tag 350 does not inadvertently also move the catheter push tag 400.

Located underneath the guidewire push tag 350 is the catheter push tag 400. The catheter hub 102 can also be located underneath the catheter push tag 400. Thus, in an example, the catheter push tag 400 and the catheter hub 102 can be said to be located subjacent the guidewire push tag 350. In this state, the catheter tube 104 and the needle 108 extend past the support piece 250 and extend distally of the nose section 215 or distal end of the housing 200. The needle tip 108a extends beyond the distal opening 104a of the catheter tube 104 in the ready position for cannulation. Rearward or proximally of the guidewire push tag 350 and the catheter push tag 400, the integrated catheter push tag 500 is covered by the back cover 600. Accordingly, the only push tag that is readily accessible to a user in this initial state is that of the guidewire push tag 350.

A practitioner can initiate cannulation using the needle device 100 in the initial state shown in FIG. 8 using only one hand while holding and using a visualization or vascular probe, such as a handheld Doppler ultrasound machine, with the other hand. Once initial placement of the needle tip is made and blood flash back is confirmed, the user can initiate the next step.

Figure 9:
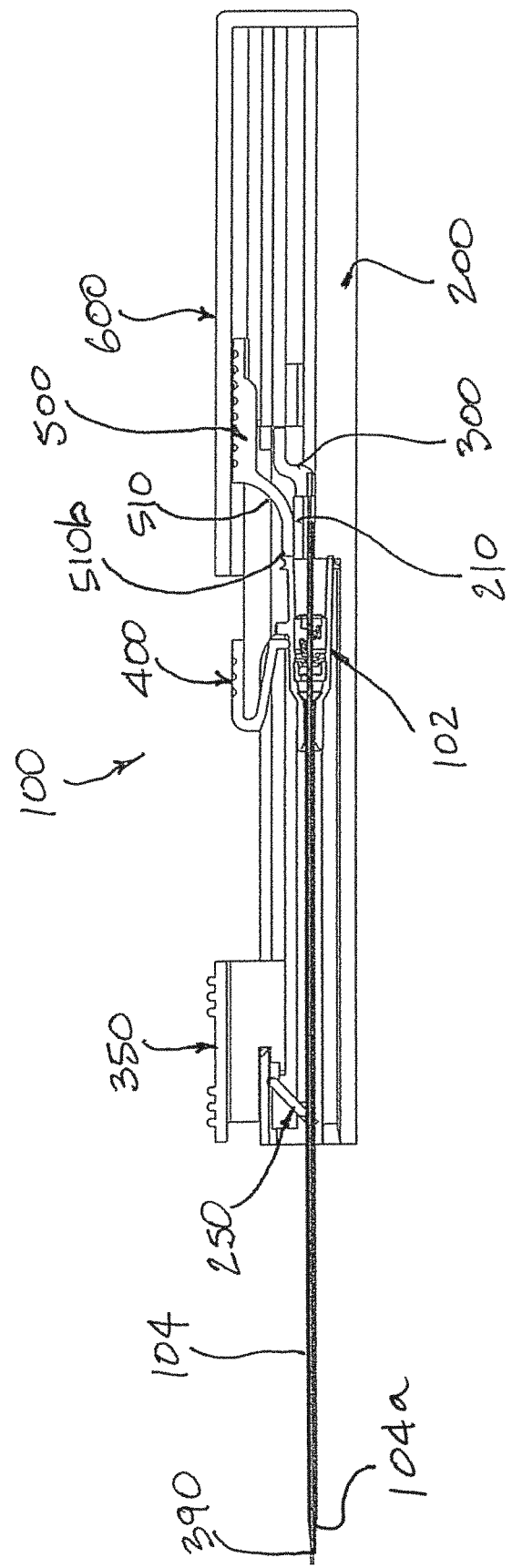
FIG. 9 shows a second state where the guidewire push tag has been manipulated.

FIG. 9 illustrates a second state where the guidewire push tag 350 has been manipulated such that it has been slidably actuated towards the distal direction. This may occur after cannulation into a vein. The guidewire push tag 350 is slidably moved to a position nearer the distal end of the housing 200. As such, the bracket 300 coupled to the guidewire push tag 350 is similarly moved by the guidewire push tag 350 so that the guidewire holder 308 (FIG. 3) can contact the retention block 210 to limit further travel. Due to this movement, the guidewire 390 is also advanced further distally. In other examples, the body of the guidewire push tag 350 abuts a surface or structure of the housing 200 to limit further distal advancement of the guidewire push tag, and hence the guidewire holder 308.

The guidewire 390 can be used in this case to aid in guidance of the catheter tube and also to prevent double puncture of the vein, especially for relatively longer catheter tube.

In the second state shown in FIG. 9, the distal movement of the guidewire push tag 350 has now exposed the catheter push tag 400, which is coupled to the catheter hub 102, the body section 403 and the integrated catheter push tag 500, which has a push leg 510 with a pushing end 510b for pushing the proximal end of the catheter hub 102. Accordingly, the catheter push tag 400 is now accessible for manipulation, such as to grip by a user and advanced in the distal direction. However, the integrated catheter push tag 500 is still covered by the back cover 600 in this second state as the catheter push tag 400 has not yet been activated, such as being moved in the distal direction. Thus, as shown in FIG. 9, the integrated catheter push tag 500 cannot be moved, because it is covered by the cover 600, until after the first catheter push tag 400 is moved distally, to then mover the integrated catheter push tag 500 distally of the distal edge of the cover 600 to be exposed.

Figure 10:
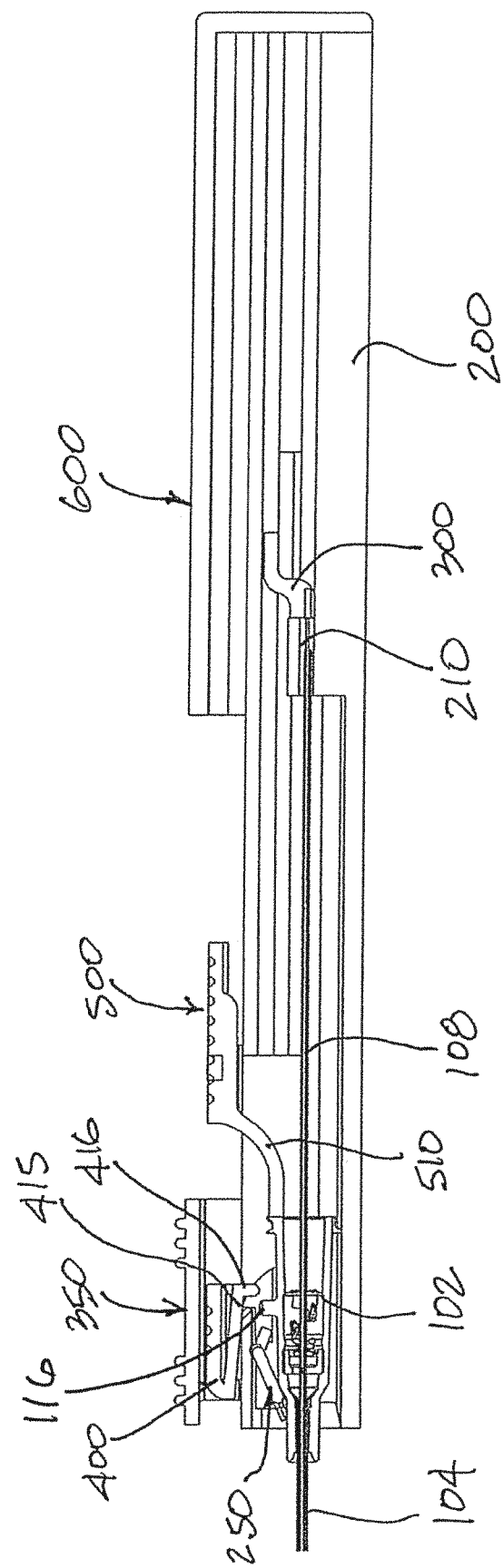
FIG. 10 shows a third state where the catheter push tag has been manipulated.

FIG. 10 illustrates a third state where the catheter push tag 400 has been manipulated such that it has been slidably actuated towards the distal direction, which initially moves the catheter hub 102 via the push leg 510 of the integrated catheter push tag 500, which is connected to the catheter push tag 400 (FIG. 2). Between the position of the catheter push tag 400 shown in FIG. 9 and in FIG. 10, the catheter push tag 400 is first pushed by a user in the distal direction to just before the catheter push tag 400 slides under the guidewire push tag 350 shown in FIG. 10, which then exposes the integrated catheter push tag 500 from the cover 600. The user then moves his or her grip from the catheter push tag 400 over to the integrated catheter push tag 500 to advance the integrated catheter push tag 500 further distally.

In one example, the catheter push tag 400 remains exposed just proximal of the guidewire push tag 350 following advancement of the catheter push tag 400 by the user or practitioner. But when the integrated catheter push tag 500 is advanced distally after being exposed from the cover 600 by distal movement of the catheter push tag 400, the body of the integrated catheter push tag 500 moves independently relatively to the catheter push tag 400 about the rails or tracks of the body section 403 (FIG. 2) until the two push tags 400, 500 contact, at which point further advancement of the integrated catheter push tag 500 pushes both bodies distally. In other example, the catheter push tag 400 is moved to its distal position shown FIG. 10 by first moving the head section 401 to advance the catheter push tag 400.

When further movement is obstructed by the guidewire push tag 350, the user can reposition his grip to push on the proximal edge or proximal end of the head section of the catheter push tag 400 to continue to advance the head section of the catheter push tag 400 under the guidewire push tag 350. Then when the device is in the position shown in FIG. 10, the user can adjust his or her grip onto the integrated catheter push tag 500 to advance the integrated catheter push tag 500.

In the third state of FIG. 10, the catheter hub 102, or at least the majority of the catheter hub, is still located within the housing 200 but has started to be released, with the nose section of the catheter hub 102 being exposed distally of the housing 200 and distally of the support piece 250. As the catheter push tag 400 moves distally, the back bent leg 415 (FIG. 4) extending from the catheter push tag 400 is pushed distally against the top surface 230 (FIG. 1) of the housing 200 and is defected upwardly by the top surface 230. The compression of the back bent leg 415 biases the retaining portion 416 at the end of the leg 415 upward and away from the catheter hub to allow the retaining portion 416 to clear the push tab 116 on the catheter hub 102. At the same or about the same time, the support piece 250 (FIG. 5), which was previously activated and rotated about the axis defined by the two mounting pins 252 when the guidewire push tag 350 is advanced, provides clearance or space for the catheter hub 102 to move distally of the support piece.

Figure 11:
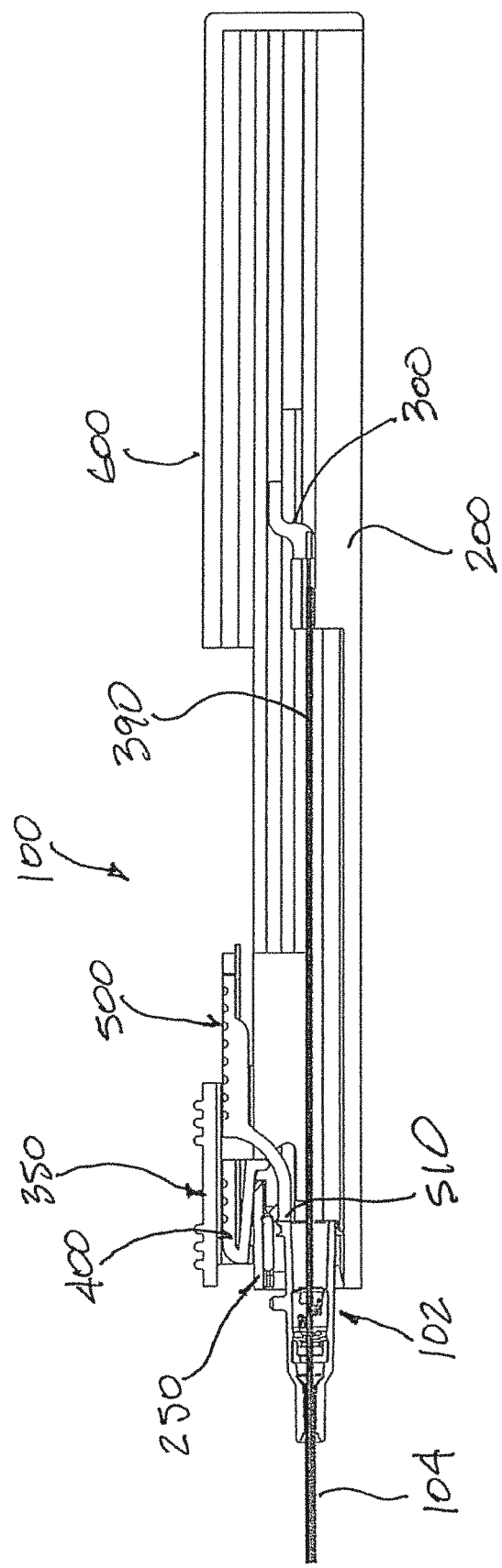
FIG. 11 shows a fourth state where the integrated catheter push tag has been manipulated.

FIG. 11 illustrates a fourth state where the integrated catheter push tag 500 has been manipulated such that it has been slidably actuated in the distal direction. In so doing, the push leg 510, and more particularly the pushing end 510b (FIG. 4), depending from the integrated catheter push tag 500 pushes the proximal end of the catheter hub 102 in the distal direction. As the catheter hub 102 can now clear the retaining portion 416 connected to the catheter push tag 400 when moving in the axial distal direction, the integrated catheter push tag 500 can push the catheter hub distally away from the housing 200 to separate from the housing.

Figure 12:
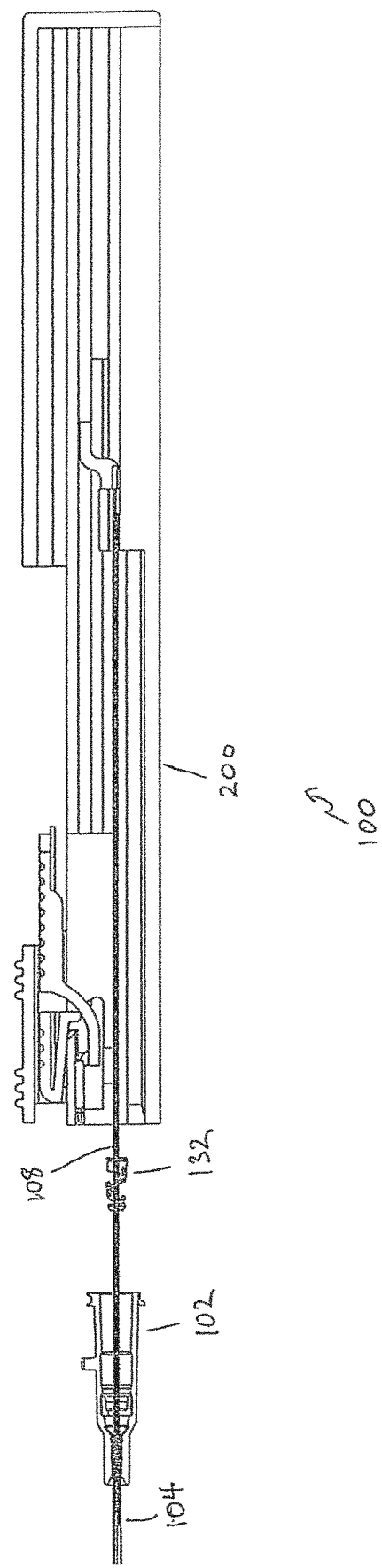
FIG. 12 shows a fifth state where the catheter hub is separated from the assembly.

FIG. 12 illustrates a fifth state where the catheter hub 102 is separated from the rest of the assembly 100. As the housing 200 and the various components assembled thereto increasingly separate from the catheter hub 102, the needle 108 and the guidewire are withdrawn from the proximal end of the catheter hub 102. As the needle moves proximally to separate from the catheter hub 102, a change in profile 144 provided near the needle tip of the needle 108, such as a radial projection on the hollow needle, a crimp, or a material buildup, engages the safety shield 132, such as an opening on a proximal wall of the safety shield, to retract the safety shield 132 from the catheter hub with the needle 108. In this position, the needle shield 132 covers the needle tip but the guidewire can still extend out the distal opening of the needle. Thus, only the catheter hub and catheter tube are left in place with the patient when the needle and the guidewire are removed. Optionally, a valve and a valve opener can be provided with the catheter hub to stop fluid flow to or from the catheter hub, such as to stop blood flashback to enable coupling of an infusion line to the catheter hub. A valved catheter assembly with a valve and a valve opener are disclosed in U.S. Pat. No. 8,333,735, the contents of which are expressly incorporated herein by reference for all purposes. FIGS. 4 and 4A show a valve 88 located inside the interior of the catheter hub 102. The valve 88 can have a disc portion and a skirt portion extending from the disc portion. The disc portion can have one or more slits, such as three slits and three flaps. The valve can block blood flowing through the catheter tube and into the catheter hub following catheterization.

Aspects of the present invention can be understood to include a catheter assembly comprising: a housing; a catheter hub; a catheter tube coupled to the catheter hub, the catheter tube defining a catheter axis; a needle projecting through the catheter tube; and two or more push tags, including a first catheter push tag. The first catheter push tag can be slidably mounted to the housing. The first catheter push tag can move the catheter hub relative to the housing, wherein a portion of the first catheter push tag can be arranged to be activated in a ready to use state.

In practice, the housing can first move to insert the needle and the catheter tube into a vein. Then after blood flash back is confirmed, the first catheter push tag can be activated.

In some examples, the catheter assembly can be practiced without a guidewire and without a guidewire push tag.

The housing can have spaced apart sidewalls. The sidewalls of the housing can form a frame or body of the housing. The housing can have a generally U-shaped structure. In some examples, part of the housing can have a full continuous circumference. In other words, part of the housing can have a structure to complete the U-shaped structure so that the housing is continuous along a radial circumference.

In an alternative embodiment, a guidewire push tag connected to a guidewire is incorporated with the catheter assembly, which can be a midline device or an extended dwell peripheral catheter assembly. The guidewire push tag can be pushed or moved to advance a guidewire after initial puncture of the needle and the catheter tube into a vein and prior to moving the first catheter push tag to advance the catheter hub.

In yet other aspects of the present invention, a midline device or an extended dwell peripheral IV device is provided and wherein the device has multiple moving parts located inside a cavity of a housing. The multiple moving parts can be configured for placing a catheter tube in a vein of a patient, said multiple moving parts being arranged sequentially by stacking different tags associated with the different moving parts. The different moving parts can be configured to move serially or sequentially, one after another. The serially movable configuration of the multiple moving parts can be configured to properly move one part of the device before the next part of the device is moved for proper device operation.

In an example, the serially movable configuration of the multiple moving parts is configured as an aid to direct a user on the appropriate way to operate the device to avoid confusion. The serially stacking of the multiple moving parts can limit early activation of a part before another part.

In an example, the serially movable configuration of the multiple moving parts can be arranged with a distally most positioned moving part, then a next distally most positioned moving part, then a next distally most positioned moving part, as so forth.

In another example, the serially movable configuration of the multiple moving parts can be arranged with two movable push tags that are arranged at approximately the same distal position on the device but wherein one is located superjacent or above the other. Thus, one moving part is configured to move first to expose the one located below.

In an example, a first moving part is exposed in a ready to use position but one or more additional moving parts to be moved are covered until after the first of the moving parts has been moved. After the first of the moving parts is moved, the second of the moving parts is exposed to be moved by a user. Optionally, a third of the moving parts is then exposed for moving by the user. Optionally, a fourth of the moving parts is then exposed for moving by the user. Optionally, a fifth of the moving parts is then exposed for moving by the user.

In an example, the moving parts are configured to move serially by staggering different push tags so that one push tag has to move before the next push tag can move, and so forth. In a particular example, a guidewire push tag is first moved, which then exposes a first catheter push tag. The first catheter push tag is then moved to expose a second catheter push tag. The second catheter push tag, or third push tag to be moved, can then move to separate a catheter hub from a housing of the midline device or extended dwell peripheral IV device. In other examples, a fourth push tag and/or a fifth push tag are moved after the third push tag is moved.

In another example, the moving parts are configured to move serially by staggering different push tags so that one push tag has to move before the next push tag can move, and so forth. In a particular example, the housing is first moved to insert the needle and the tip of the catheter tube into the vein. Blood flash back is observed, such as through a notch near the needle tip or an elongated groove that extends lengthwise of the needle between the needle and the catheter tube. Once blood flash back is confirmed, the housing is held steady and the guidewire push tag is first moved, first among the various movable components mounted to the housing, which then exposes the first catheter push tag. The first catheter push tag is then moved to expose the second catheter push tag. The second catheter push tag, or generically the third push tag to be moved, can then move to separate a catheter hub from a housing of the extended dwell peripheral IV device. In other examples, a fourth push tag and/or a fifth push tag are moved after the third push tag is moved. For example, fourth and fifth push tags can be used to help push the catheter hub away from the housing and to separate the housing into two pieces or more pieces.

In yet another example, a guidewire and a guidewire push tag are not incorporated with the midline device. However, the midline device can have at least two catheter push tags, which can include a first catheter push tag and a second catheter push tag, and wherein the first catheter push tag is first moved to expose the second push tag, which can then be moved by a user.

The catheter device can further comprise a guidewire projecting through the needle; and a guidewire push tag for moving the guidewire relative to the housing. The guidewire can be optional and may be incorporated when the length of the needle and catheter tube warrants its use.

In an example, a retention block is provided inside the housing to hold or secure the needle. The retention block can be fixed to the housing. The retention block can be attached and fixed to the housing. The retention block can be molded or unitarily formed with the housing. The retention block can have a body with a through bore having a first open end and a second open end.

The needle can extend distally of the first open end. The guidewire can project through the second open end and into the needle.

The guidewire can be held by a guidewire holder. The guidewire holder can be part of a bracket or frame. The bracket can be secured to or fixed to the guidewire push tag. The bracket can be fixed to an extension that extends from a wall surface of the guidewire push tag.

Movement of the guidewire push tag can move the bracket and can move the guidewire holder. The guidewire holder can abut the retention block to stop distal advancement of the guidewire.

The catheter assembly can further comprise a second catheter push tag to release the catheter hub from coupling with the housing.

The second catheter push tag can be slidably coupled to the first catheter push tag.

In an example, when the first catheter push tag is moved, the movement of the first push tag also moves the second push tag to expose the second push for moving by a user.

A guidewire push tag, when incorporated, can prevent user manipulation of the first catheter push tag in a ready to use state. In an example, the guidewire push tag, when incorporated, covers the first catheter push tag so that the guidewire push tag is to be moved first to expose the first catheter push tag.

In an example, the guidewire push tag, when incorporated, overlies the first catheter push tag and covers the first catheter push tag. In a particular example, the guidewire push tag is moved in a distal direction to expose the first catheter push tag. The first catheter push tag can remain in place while the guidewire push tag is moved. Movement of the guidewire push tag can be in the distal direction.

Movement of the first catheter push tag can be in the distal direction.

Movement of the second catheter push tag can be in the distal direction.

Movement of the first catheter push tag can be prevented by the guidewire push tag.

Movement of the first catheter push tag can move a structure that connects the first catheter push tag with the second catheter push tag.

The second catheter push tag can be covered until after the first catheter push tag is moved in the distal direction.

The housing can prevent use manipulation of the second catheter push tag in a ready to use state. In an example, a cover attached to a frame of the housing can be part of the overall housing. The cover can snap fit to the housing, such as with detents. The cover can be glued, bonded, or welded to the housing. The cover can be utilized to cover the second catheter push tag when the first catheter push tag is in its proximal position, prior to the first catheter push tag being moved by a user.

In an example, a midline device or an extended dwell peripheral IV device is provided with a guidewire push tag, a first catheter push tag, and a second catheter push tag. In a particular example, the guidewire push tag covers the first catheter push tag from being touched by a user and a cover or cap mounted with the frame of the housing covers the second catheter push tag from being touched by a user in the first or ready to use position of the device.

The first catheter push tag can be unobscured after user manipulation of the guidewire push tag; and wherein the second catheter push tag can be unobscured after user manipulation of the first catheter push tag.

The first catheter push tag, the guidewire push tag, and the second catheter push tag can be stacked within the housing such that only the guidewire push tag is accessible in the ready to use state.

Aspects of the present disclosure include a method of assembling or making a catheter assembly. The method can comprise assembling a first catheter push tag to a housing, wherein a portion of the first catheter push tag is obscured in a ready to use state; placing a catheter hub in sliding contact with the first catheter push tag; coupling a catheter tube to the catheter hub; projecting a needle through the catheter tube.

The method can further comprise projecting a guidewire through the needle and placing a guidewire push tag into the housing to move the guidewire relative to the housing.

The method can comprise coupling a guidewire to a guidewire push tag and positioning the guidewire push tag to overlie the first catheter push tag.

The method can comprise placing a needle into the housing and securing the needle to a retention holder or block.

The method can comprise mounting a first catheter push tag coupled with a second catheter push tag to the housing.

The method can comprise placing a catheter hub coupled with a catheter tube in sliding contact with the first catheter push tag so that movement of the first catheter push tag will cause the catheter hub to move.

The method can comprise placing the needle through the catheter hub and the catheter tube.

The method can comprise projecting a guidewire through the needle and placing a guidewire push tag into the housing to move the guidewire relative to the housing.

The present invention further includes a method of using a catheter device described elsewhere herein.

After initial insertion of the needle tip for vascular access and if the device incorporates a guidewire, the guidewire push tag can be advanced by a user to advance the guidewire relative to the needle tip. As is well understood in the industry, the guidewire can be utilized to enter tight spaces or to assist in inserting, positioning, and/or moving the catheter deeper into the vein.

The method can further comprise mounting a second catheter push tag relative to the first catheter push tag, said second catheter push tag can be configured to release the catheter hub from the housing.

The second catheter push tag can be slidably coupled to the first catheter push tag.

The guidewire push tag can prevent user manipulation of the first catheter push tag in a ready to use state.

Figure 13:
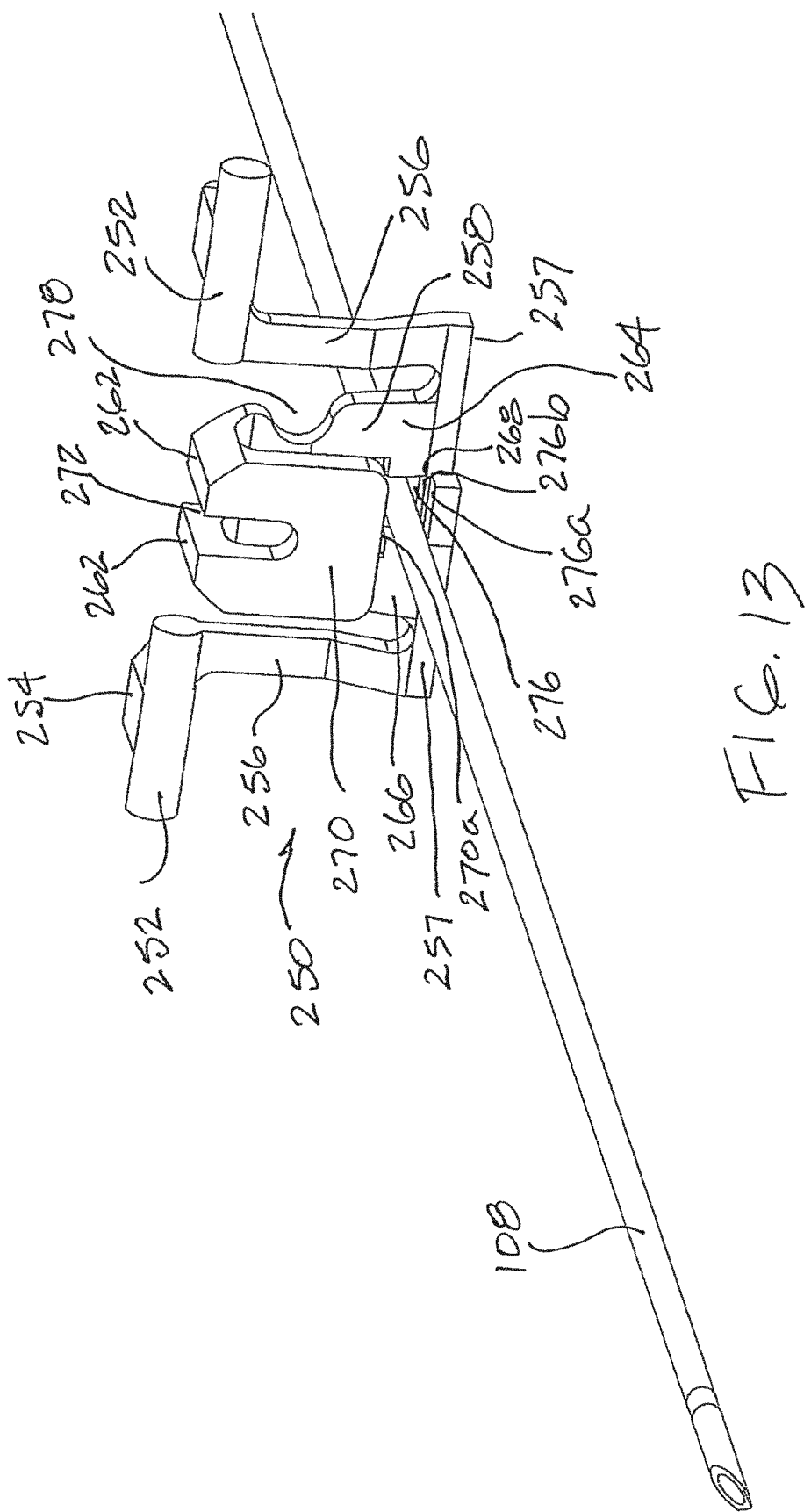
FIG. 13 shows a perspective view of another exemplary embodiment.
Figure 14:
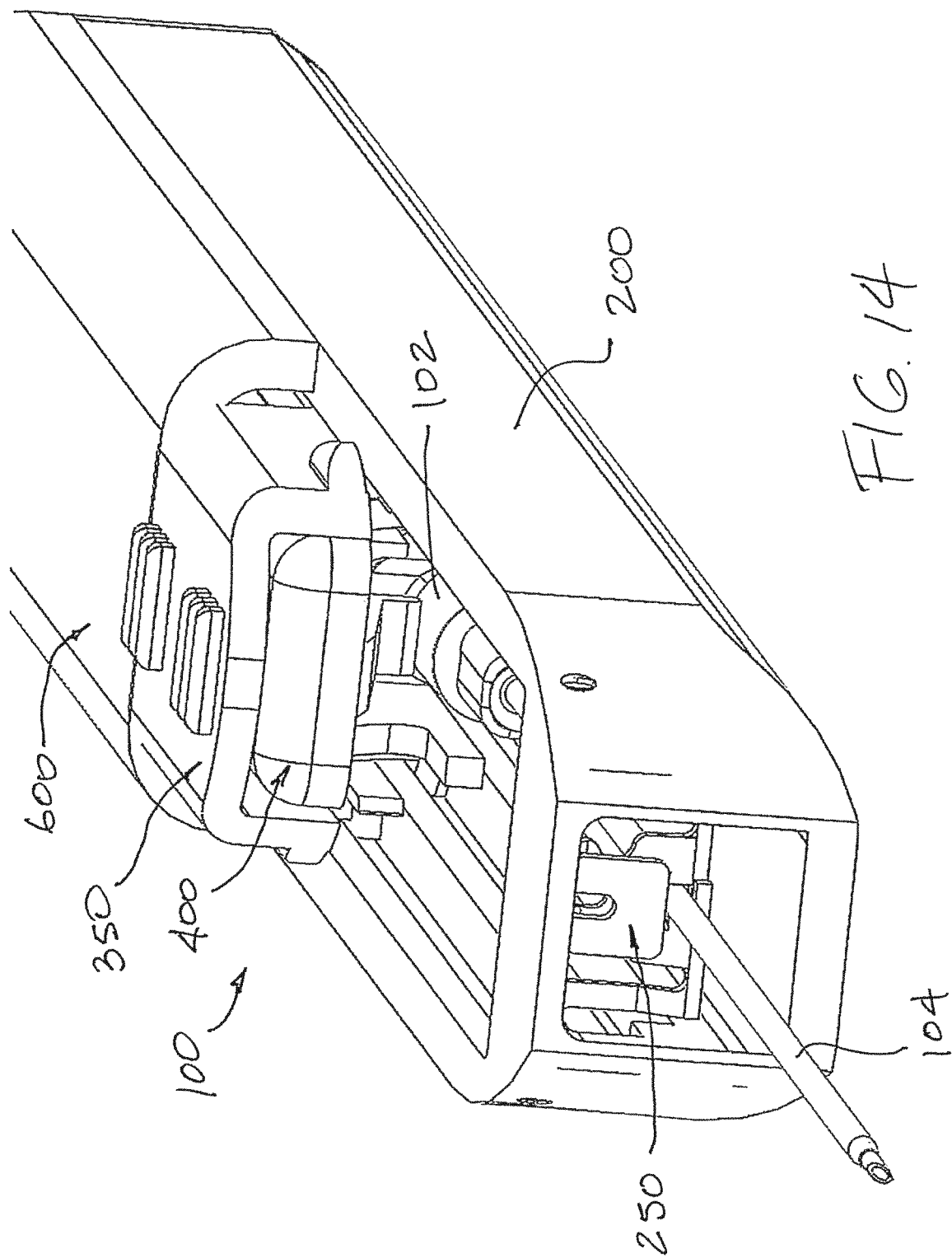
FIG. 14 shows the passive release front gate as applied in an assembly.

FIGS. 13 and 14 illustrate an exemplary alternative embodiment of a support piece 250 and can be assembled in a similar manner as shown in FIGS. 5 and 7. The present exemplary support piece 250 can be considered a passive release front gate plate.

FIG. 13 illustrates a perspective view of the exemplary embodiment. The support piece 250 of the present embodiment can have a central portion with biasing, resilient, or springing properties as part of the central body. The support piece 250 can have a folded over body piece 258 and two side arms 256 that are attached to the central body 258 by two connecting or joining portions 257. The present support piece 250 can be used in a similar manner as other support pieces described elsewhere herein and usable with the midline catheter assembly disclosed with reference to FIGS. 1-12.

The central body portion or piece 258 can be defined by a continuous portion of material that is bent and shaped to provide spring like characteristics. From each side arm 256, the support piece 250 can have a joining section 257 connected to the body portion 258. The body portion 258 has an overlapping first body portion 264 having a wall or surface that overlaps with a wall or surface of a second body portion 266, which has a split or seam 268 therebetween that can separate or open up by deflecting upon advancement of the guidewire push tag 350, which incorporates actuations bars 381 (FIG. 5) to press the two rotation stops 254 on the two mounting pins 252 inwardly to facilitate separation at the seam, as previously discussed. With the first and second body portions 264, 266 deflected and separated by the guidewire push tag, subsequent advancement of the catheter hub will further deflect the support piece 250 to further open up to allow the catheter hub to pass therethrough. A cut-out 278 can be provided on each of the first body portion 264 and the second body portion 266 to reduce rigidity to the two body portions 264, 266 to allow them to more readily deflect when pushed by the catheter hub.

The first body portion 264 and the second body portion 266 are joined by a folded over flap 270. The folded over flap 270 has a cut-out 272 to define two bent sections 262. The first and the second body portions 264, 266 are provided with a guide passage 276 and guiding edges 276a, 276b. The fold over flap 270 has a support edge 270a. The catheter tube 104 and needle 108 can pass through the guide passage 276 and be supported by the support edge 270a on the folded over flap and the two guiding edges 276a, 276b, which can limit or help prevent kinking. In some examples, the fold over flap 270 can be made thin or short to reduce the physical structure of the flap to decrease the force necessary to deflect the first and second body portions 264, 266.

Accordingly, the catheter tube 104 can be inserted through the guide passage 276. As the first body portion 264 is separated from the second body portion 266 except at the two bent sections 262 that join the folded over flap 270, the relationship between the first and second body portions can be used to apply a biasing force against the catheter tube 104 and to deflect when pushed by the catheter hub.

FIG. 14 illustrates the passive release front gate 250 of FIG. 13 as applied in a needle device assembly or extended dwell catheter assembly 100, similar to FIG. 7, to support the catheter tube 104 and the cannula located inside the catheter tube.

Figure 15:
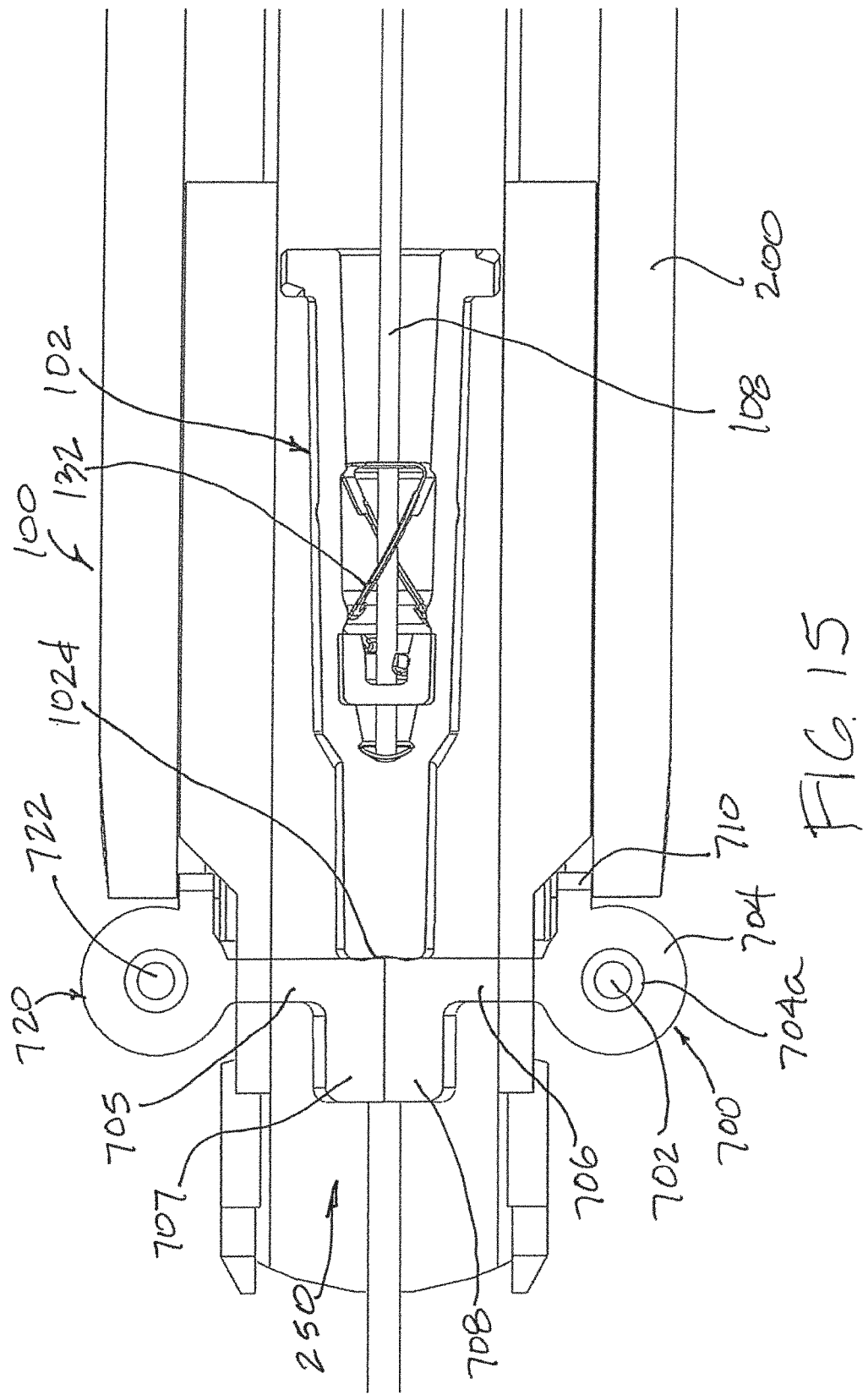
FIG. 15 shows a plan view of a pair of gates for stabilization of the needle during cannulation in an un-activated position.
Figure 16:
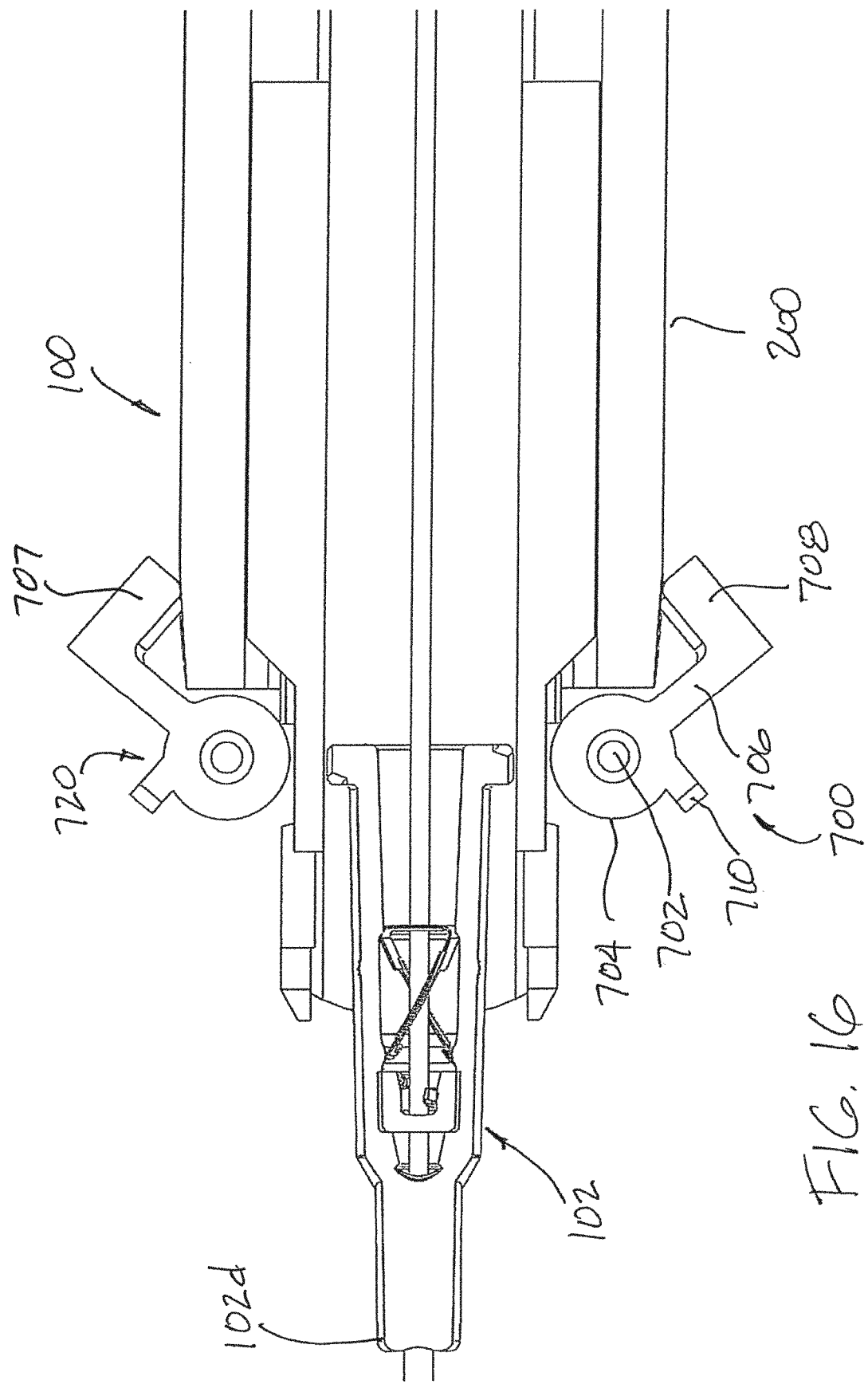
FIG. 16 shows a plan view of a pair of gates in an activated position to allow for release of the catheter from the assembly in accordance to further aspects of the invention.
Figure 17:
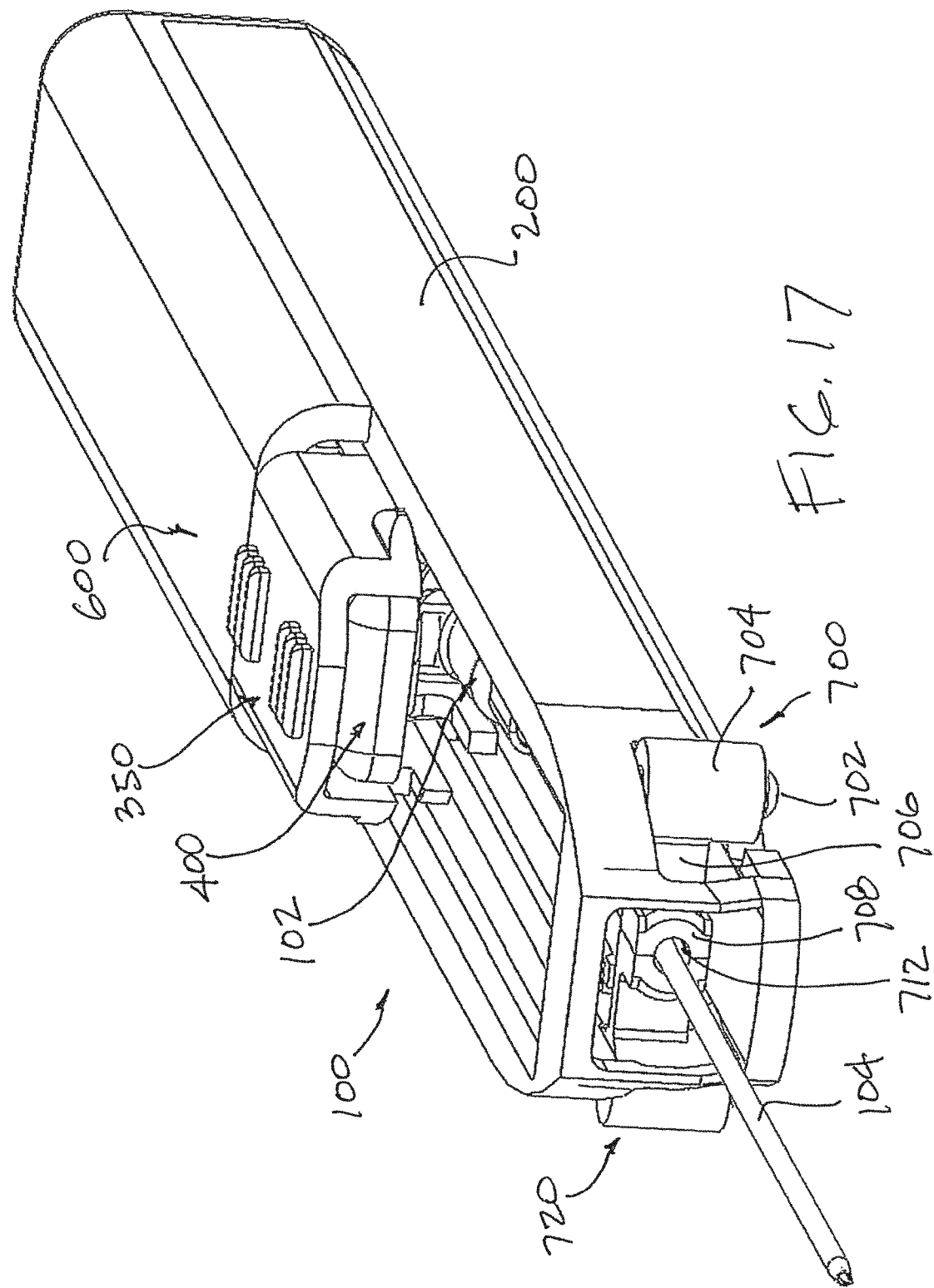
FIG. 17 shows a perspective view of an exemplary embodiment of an extended dwell catheter assembly in an assembled state.
Figure 1B:
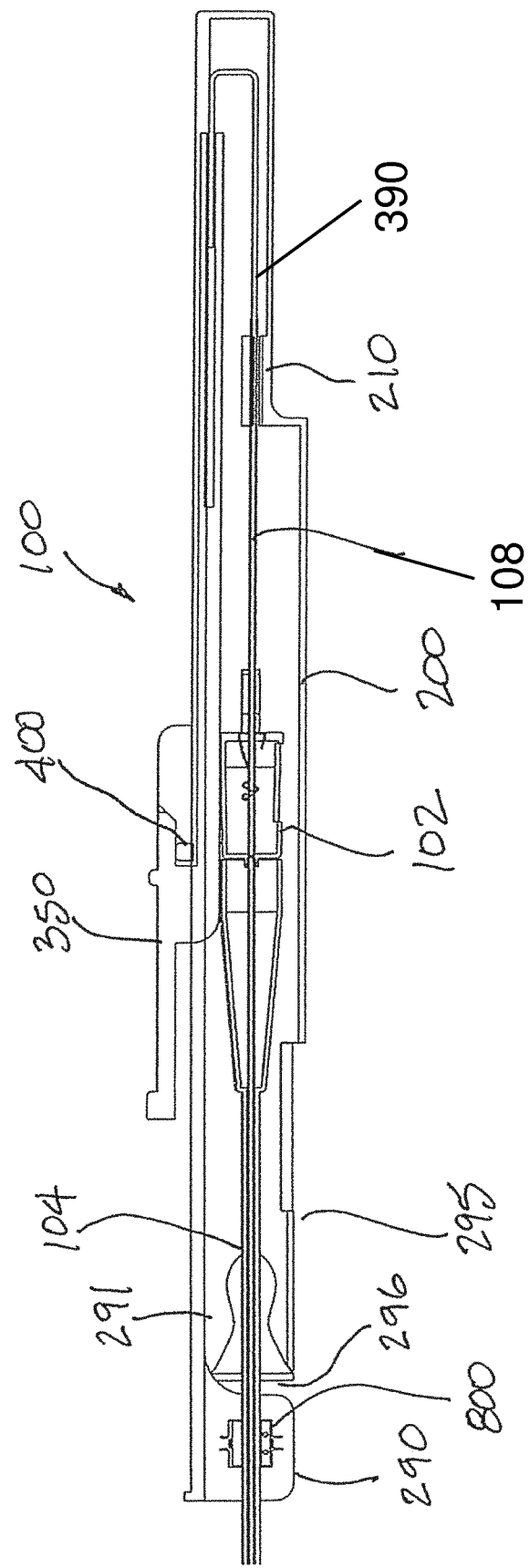

FIGS. 15-17 illustrate an exemplary embodiment of a support piece 250 variant. In the present embodiment, the support piece 250 has a passive release front gate and is coupled to the housing 200 of the extended dwell catheter assembly 100, which can be similar to the extended dwell catheter assemblies discussed elsewhere. FIG. 15 shows a top plan view of a pair of gates 700, 720 for supporting the needle 108 and catheter tube 104 during cannulation, shown in an un-activated position. The two gates 700, 720 are generally symmetrical about a centerline of the assembly 100. Thus, where features are discussed with respect to one of the gates 700, the same features are understood to be reflective of the other gate 720.

The pair of gates 700, 720 can rotate around respective pivot points 702, 722 that are spaced from the centerline of the assembly 100. Each of the gates 700, 720 can have a substantially L shape structure with a base portion 705 and an extended portion 707 forming the L shape. Each of the gates has a cylindrical portion 704 with a boss 704a surrounding the pivot point 702, such that the boss 704a is concentric with the pivot point 702. Extending in a radial direction from the cylindrical portion 704, a radially outward projection arm 706, forming part of the base 705, can be coupled with a gate portion 708, which forms part of the extended portion 707 of the generally L shape structure. Substantially perpendicular to the projection arm 706, there can be a rotation stop 710 that projects in the radial direction from the surface of the cylindrical portion 704 offset from the center point or pivot point 702.

The projection arm 706 can have a substantially rectangular cross section as it extends in the radial direction from the cylindrical portion 704. The gate portion 708 can have a larger cross-sectional area than the projection arm 706 when viewed perpendicular to the centerline of the assembly 100.

As shown in FIG. 17, it is envisioned that the gate portion 708 of each of the pair of gates 700, 720 can have an opening or recess 712 sized to fit the catheter tube 104. As shown, each gate portion 708 can have a shape of a half or partial hollow cylinder.

FIG. 16 illustrates a plan view of the pair of gates 700, 720 of FIG. 15 in an activated position to allow for the release of the catheter hub 102 from the assembly 100. As shown, when the catheter hub is desired to be released, the distal tip 102d acts on the gate portions 707, 708 of the pair of gates, which can previously be released by advancing the guidewire push tag 350 to press against the two rotational stops 710 to allow the two gate portions 707, 708 to partially open. The pair of gates can then rotate outwardly further by the advancing hub to unblock the path for the catheter hub 102 to allow separation of the catheter hub from the rest of the assembly 100. In an example, the pair of gates 700, 720 can rotate freely following activation by the guidewire push tag 350, which is advanced before the catheter push tag 400, as previously discussed with reference to FIGS. 8-12.

Figure 19:
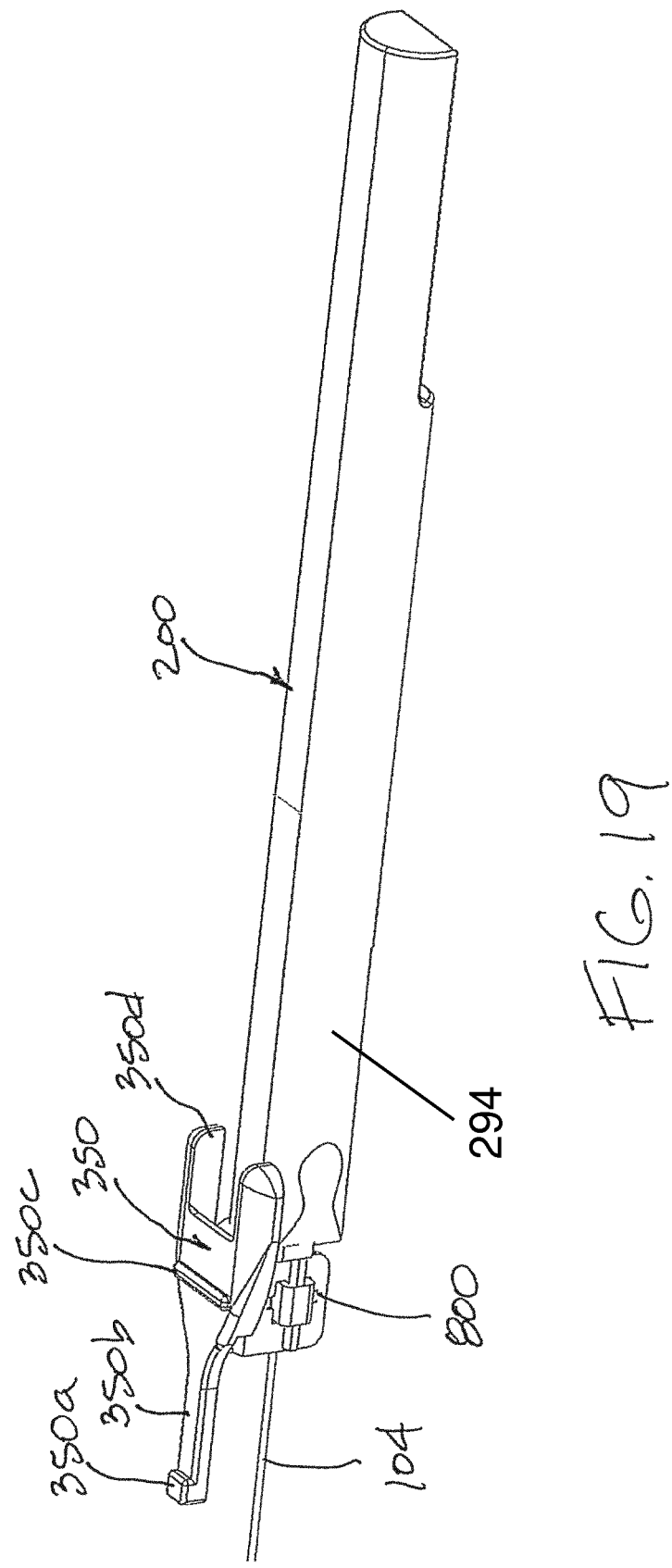
FIG. 19 shows an exemplary embodiment of the guidewire push tag.

FIGS. 18-20 illustrate an exemplary embodiment of an extended dwell catheter assembly 100 in accordance to further aspects of the invention. The catheter assembly 100 can include a housing 200, a catheter hub 102, a catheter tube 104, a support piece 800 that can embody a pin head, a guidewire push tag 350 with guidewire, a needle 108, a needle guard, and a catheter push tag 400.

The housing 200 can have a main section 291 and a distal section 290. The main section 291 can be substantially rectangular in shape. The distal section 290 extends from a connecting side wall 294 of a distal end of the main section 291. The distal section 290 does not continuously extend from at least one adjacent side wall 295 to the connecting side wall 294, thereby defining a gap 296 between the distal section 290 and the main section 291. The distal section 290 can be narrower in width than the main section 291. The distal section 290 can also be substantially rectangular or U-shape.

FIG. 18 illustrates an un-activated, assembled, exemplary embodiment of the catheter assembly 100 of the present alternative embodiment.

A guidewire 390 can be advanced by manipulation of the guidewire push tag 350 on the top of the main section 291 of the housing 200. The housing 200 can additionally have a retention block 210 for attaching the needle 108 and can act as a distal stop for the guidewire 390. The catheter hub 104 is guided by a support piece 800, which can have one or more projections with each having a pin head-like shape. When the catheter push tag 400 is manipulated forward to the distal end, the movement can allow for the catheter to disengage from the pin head from the bottom of the assembly 100.

FIG. 19 illustrates an exemplary embodiment of the guidewire push tag 350. The push tag 350 can be used as an exemplary embodiment for a push tag for manipulation. The guidewire push tag 350 can have a distal narrow portion 350a attached to a narrow distal arm 350b. The distal arm 350b can taper into a main body section 350c, which is itself coupled with a proximal end with two opposed extrusions 350d.

In a position where the guidewire 390 is extended, the guidewire push tag 350 can overlap with the pin head support piece 800.

FIG. 20 illustrates a perspective view from the bottom of the assembly 100. The catheter can be detached from the bottom of the pin head 800.

Methods of making and of using extended dwell catheter assemblies and their components as described herein are within the scope of the present invention.

Although limited embodiments of the catheter assemblies and their components have been specifically described and illustrated herein, many modifications and variations will be apparent to those skilled in the art. For example, the various parts of the valve may incorporate alternate materials, etc. Furthermore, it is understood and contemplated that features specifically discussed for one catheter assembly embodiment may be adopted for inclusion with another embodiment, provided the functions are compatible. Accordingly, it is to be understood that the valve and its application in catheter assemblies constructed according to principles of the disclosed device, system, and method may be embodied other than as specifically described herein. The disclosure is also defined in the following claims.

What is claimed is:

1. A catheter assembly comprising:
a housing having a plurality of walls including two spaced apart sidewalls;
a catheter hub located within the housing;
a catheter tube coupled to the catheter hub, the catheter tube defining a catheter axis;
a needle having a needle tip projecting through the catheter tube with the needle tip exposed at a distal end of the catheter tube; and
a catheter activation device comprising a first push tag having a surface for pushing to move the catheter hub relative to the housing and a second push tag having a surface for pushing to move the catheter hub relative to the housing,
wherein the first and second push tags are movable with one another to move the catheter hub from a first position to a second position within the housing and the first and second push tags are movable relative to one another for moving the catheter hub from the second position to a third position; and
wherein the first and second push tags are spaced from one another a first distance in the first position, in which the second push tag is inaccessible for pushing, and the first and second push tags are spaced from one another a second distance in the second position, which differs from the first distance and in which the second push tag is accessible for pushing.

2. The catheter assembly of claim 1, wherein the surface of the second push tag is obscured by the housing in a ready to use state.

3. The catheter assembly of claim 2, wherein a cover attached to the housing obscures the surface of the second push tag and making the second push tag inaccessible in the first position.

4. The catheter assembly of claim 1, further comprising:
a guidewire projecting through the needle; and
a guidewire push tag slidably mounted within the housing for moving the guidewire relative to the needle.

5. The catheter assembly of claim 4, wherein the guidewire push tag covers the first push tag in the first position.

6. The catheter assembly of claim 1, wherein the second push tag is slidably coupled to the first push tag to move with the first push tag and slidable relative to the first push tag.

7. The catheter assembly of claim 1, wherein the first push tag, the guidewire push tag, and the second push tag are stacked within the housing such that only the guidewire push tag is accessible by a user in a ready to use state.

8. The catheter assembly of claim 1, further comprising a support piece pivotably connected at a distal end of the housing and in contact with the catheter tube.

9. The catheter assembly of claim 8, wherein the support piece is deflectable by a guidewire push tag.

10. The catheter assembly of claim 8, wherein the support piece comprises two mounting arms defining a rotational axis.

11. A method of assembling a catheter assembly, the method comprising:
assembling a catheter activation device comprising a first push tag having a surface and a second push tag having a surface to a housing, said housing having spaced apart sidewalls;
placing a catheter hub in sliding communication with the first push tag and the second push tag;
coupling a catheter tube to the catheter hub;
projecting a needle having a needle tip through the catheter tube so that the needle tip is located distally of a distal opening of the catheter tube; and
wherein the first push tag and the second push tag are movable with one another to move the catheter hub from a first position to a second position and the first push tag and the second push tag are slidable relative to one another to move the catheter hub from the second position to a third position.

12. The method of claim 11, further comprising:
projecting a guidewire through the needle;
mounting a guidewire push tag to the housing to move the guidewire relative to the housing.

13. The method of claim 12, further comprising mounting the second push tag in sliding communication with groove rails located on sidewalls of the first push tag.

14. The method of claim 13, further comprising mounting the needle to a retention block and projecting the guidewire through the retention block and through the needle.

15. The method of claim 12, further comprising mounting the needle to a retention block and projecting the guidewire through the retention block and through the needle.

16. The method of claim 11, wherein a distance between the first push tag and the second push tag is reduced when the first push tag and the second push tag slide relative to one another.

17. The method of claim 16, further comprising engaging rail protrusions of the second push tag with groove rails of the first push tag.

18. A method of assembling a catheter assembly, the method comprising:
assembling a catheter activation device comprising a first push tag having a surface and a second push tag having a surface to a housing, said housing having spaced apart sidewalls;
placing a catheter hub in sliding communication with the first push tag and the second push tag;
coupling a catheter tube to the catheter hub;
projecting a needle through the catheter tube;
further comprising mounting the second push tag in sliding communication with groove rails located on sidewalls of the first push tag; and
wherein the first push tag and the second push tag are movable with one another to move the catheter hub from a first position to a second position and the first push tag and the second push tag are movable relative to one another to move the catheter hub from the second position to a third position.

19. The method of claim 18, further comprising:
projecting a guidewire through the needle; and
mounting a guidewire push tag to the housing to move the guidewire relative to the housing.

20. The method of claim 19, further comprising mounting the needle to a retention block and projecting the guidewire through the retention block and through the needle.

21. The method of claim 18, further comprising engaging rail protrusions of the second push tag with groove rails of the first push tag.

22. A method of assembling a catheter assembly, the method comprising:
assembling a catheter activation device comprising a first push tag having a surface and a second push tag having a surface to a housing, said housing having spaced apart sidewalls;
placing a catheter hub in sliding communication with the first push tag and the second push tag;
coupling a catheter tube to the catheter hub;
projecting a needle through the catheter tube;
mounting the needle to a retention block and projecting a guidewire through the retention block and through the needle; and
wherein the first push tag and the second push tag are movable with one another to move the catheter hub from a first position to a second position and the first push tag and the second push tag are movable relative to one another to move the catheter hub from the second position to a third position.

23. The method of claim 22, further comprising mounting a guidewire push tag to the housing to move the guidewire relative to the housing.

24. The method of claim 22, further comprising mounting the second push tag in sliding communication with groove rails located on sidewalls of the first push tag.

25. The method of claim 22, further comprising engaging rail protrusions of the second push tag with groove rails of the first push tag.

* * * * *